(12) United States Patent
Nawn et al.

(10) Patent No.: US 10,980,955 B2
(45) Date of Patent: Apr. 20, 2021

(54) AIRWAY MANAGEMENT DEVICE FOR IDENTIFICATION OF TRACHEAL AND/OR ESOPHAGEAL TISSUE

(71) Applicant: THE UNITED STATES OF AMERICA AS REPRESENTED BY THE SECRETARY OF THE ARMY, Fort Detrick, MD (US)

(72) Inventors: Corinne Nawn, San Antonio, TX (US); Brian Souhan, Bethesda, MD (US)

(73) Assignee: The Government of the United States, as represented by the Secretary of the Army, Fort Detrick, MD (US)

( * ) Notice: Subject to any disclaimer, the term of this patent is extended or adjusted under 35 U.S.C. 154(b) by 203 days.

(21) Appl. No.: 16/051,540

(22) Filed: Aug. 1, 2018

(65) Prior Publication Data

US 2019/0083728 A1 Mar. 21, 2019

Related U.S. Application Data

(63) Continuation-in-part of application No. PCT/US2017/016174, filed on Feb. 2, 2017.
(Continued)

(51) Int. Cl.
*A61M 16/04* (2006.01)
*A61B 1/267* (2006.01)
(Continued)

(52) U.S. Cl.
CPC ........... *A61M 16/045* (2014.02); *A61B 1/267* (2013.01); *A61B 5/0075* (2013.01);
(Continued)

(58) Field of Classification Search
CPC .............. A61M 16/04; A61M 16/045; A61M 16/0411; A61B 1/267; A61B 1/2676;
(Continued)

(56) References Cited

U.S. PATENT DOCUMENTS

| 5,193,544 A | 3/1993 | Jaffe |
| 5,331,967 A | 7/1994 | Akerson |

(Continued)

FOREIGN PATENT DOCUMENTS

| WO | 2012058441 A2 | 5/2012 |
| WO | 2012149519 A1 | 11/2012 |

OTHER PUBLICATIONS

Nawn, C. D., Souhan, B. E., Carter, R., Kneapler, C., Fell, N. F., & Ye, J. Y. Spectral characterization of tracheal and esophageal tissues using a hyperspectral camera and fiber optic sensors. In SPIE BiOS (pp. 970212-970212). International Society for Optics and Photonics. Mar. 2016.

(Continued)

*Primary Examiner* — Joseph D. Boecker
*Assistant Examiner* — Thomas W Greig
(74) *Attorney, Agent, or Firm* — Leigh Callander; William Eshelman

(57) ABSTRACT

An airway management device (10) for a human or animal subject (20) includes an airway tube (101) having a first end for disposal external to the subject (20) and a second end (102) for disposal in a portion of an airway of the subject (20). A light emitting element (108) and a photo-sensing element (109) may be disposed at the second end (102) of the airway tube (101). The light emitting element (108) may be configured to transmit light to tissue adjacent to the light emitting element (108). The photo-sensing element (109) may be configured to receive reflectance spectra (204) from the tissue. The location of the second end (102) of the airway tube (101) may be determined from characteristics of the reflectance spectra (204) of the tissue.

35 Claims, 24 Drawing Sheets

Related U.S. Application Data

(60) Provisional application No. 62/292,277, filed on Feb. 6, 2016.

(51) Int. Cl.
*A61B 5/06* (2006.01)
*A61B 5/00* (2006.01)
*A61B 5/1459* (2006.01)
*A61B 5/08* (2006.01)
*A61B 5/083* (2006.01)

(52) U.S. Cl.
CPC ............ *A61B 5/0084* (2013.01); *A61B 5/065* (2013.01); *A61B 5/1459* (2013.01); *A61M 16/0411* (2014.02); *A61M 16/0488* (2013.01); *A61B 5/08* (2013.01); *A61B 5/0836* (2013.01); *A61B 5/4887* (2013.01); *A61M 16/0418* (2014.02); *A61M 16/0434* (2013.01); *A61M 2205/3313* (2013.01); *A61M 2205/581* (2013.01); *A61M 2205/583* (2013.01)

(58) Field of Classification Search
CPC ....... A61B 5/0075; A61B 5/0084; A61B 5/08; A61B 5/06; A61B 5/00; A61B 5/1459; A61B 5/083

See application file for complete search history.

(56) References Cited

U.S. PATENT DOCUMENTS

| | | |
|---|---|---|
| 5,560,351 A | 10/1996 | Gravenstein et al. |
| 5,775,322 A | 7/1998 | Silverstein et al. |
| 6,705,319 B1 | 3/2004 | Wodicka et al. |
| 6,961,600 B2 | 11/2005 | Kohl et al. |
| 7,942,813 B2 | 5/2011 | Mackin |
| 8,166,967 B2 | 5/2012 | Qiu |
| 8,371,303 B2* | 2/2013 | Schaner ................ A61M 16/04 128/207.15 |
| 8,479,739 B2 | 7/2013 | Hirsh |
| 2004/0039252 A1 | 2/2004 | Koch, III |
| 2010/0030133 A1 | 2/2010 | Elia et al. |
| 2010/0261995 A1 | 10/2010 | McKenna et al. |
| 2012/0116156 A1 | 5/2012 | Lederman |
| 2013/0269703 A1 | 10/2013 | Wood et al. |
| 2015/0073268 A1* | 3/2015 | Stopek ................... A61B 5/113 600/424 |
| 2015/0250423 A1 | 9/2015 | Hacker et al. |

OTHER PUBLICATIONS

Nawn, C. D., Souhan, B. E., Carter, R., Kneapler, C., Fell, N. F., & Ye, J. Y. Distinguishing tracheal tissues with hyperspectral imaging and fiber-optic sensing. Journal of Biomedical Optics, 21(11), 117004-117004. Nov. 2016.

Nawn C.D., Blackburn M.B., Souhan B.E., Kneapler C., Fell N., Ye J.Y., Carter R. Spectral Characterization of Tracheal and Esophageal Tissues. Military Health System Research Symposium, Aug. 2016. Poster.

Souhan, B.E., Nawn, C.D., Shmel, R., Watts, K.L., & Ingold, K.A. Fiber-optic tracheal detection device. Paper and Slides Presented at SPIE BiOS—Optical Fibers and Sensors for Medical Diagnostics and Treatment Applications. Jan. 2017.

Nawn, C.D., Souhan, B.E., Christensen, W., Shmel, R., Watts, K.L., & Ingold, K.A. Tracheal Detection Device. Military Health System Research Symposium. Poster Presentation. Aug. 2017.

Nawn, C.D., Blackburn M.B., Souhan B.E., Mosquera, G., Robitschek, J.M., & Hudson, I. Tracheal Detection Device for Combat Provider Feedback. San Antonio Military Health System & Universities Research Symposium. Podium Presentation. Jun. 2018.

PCT International Search Report and Written Opinion.

* cited by examiner

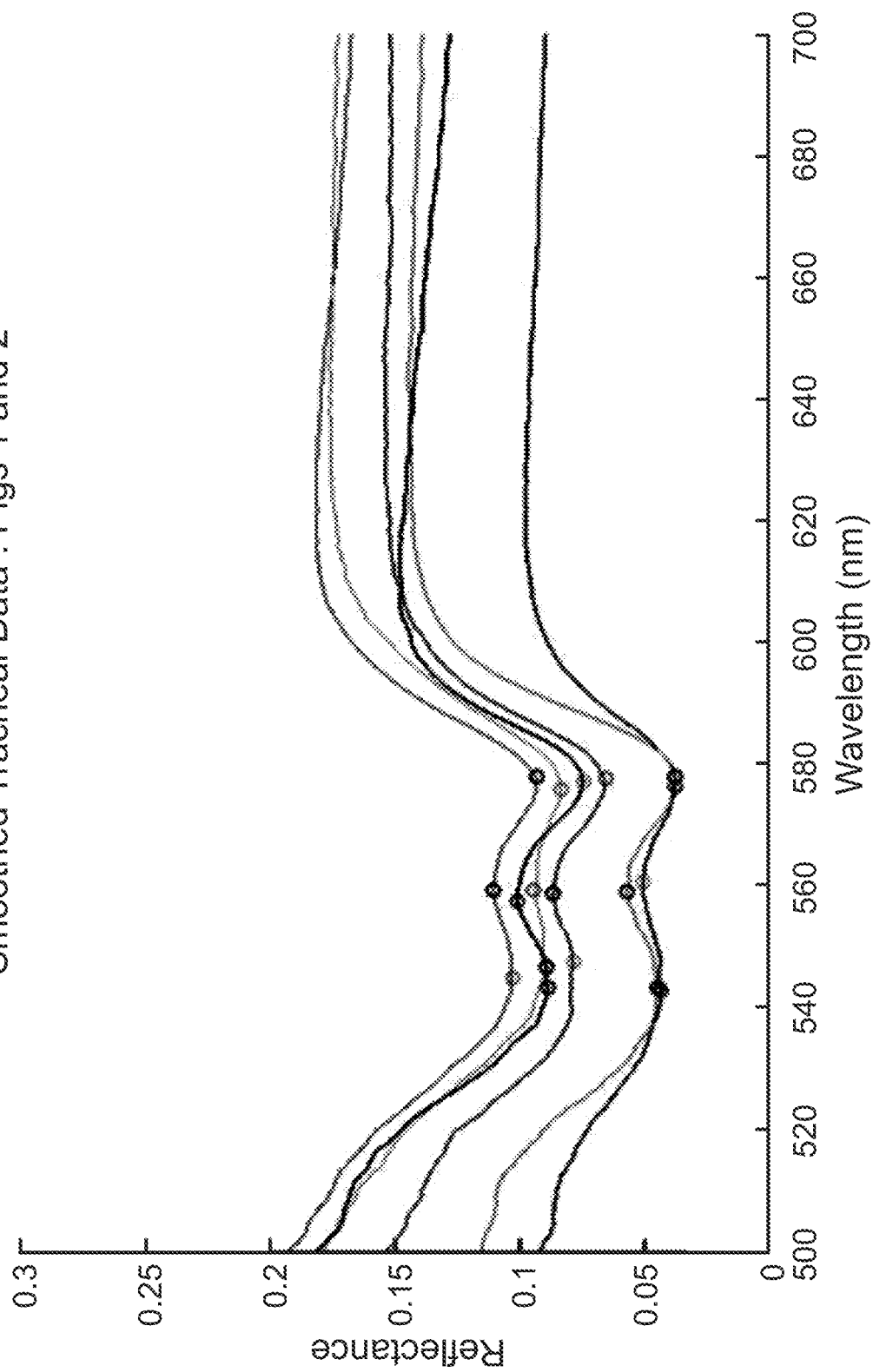

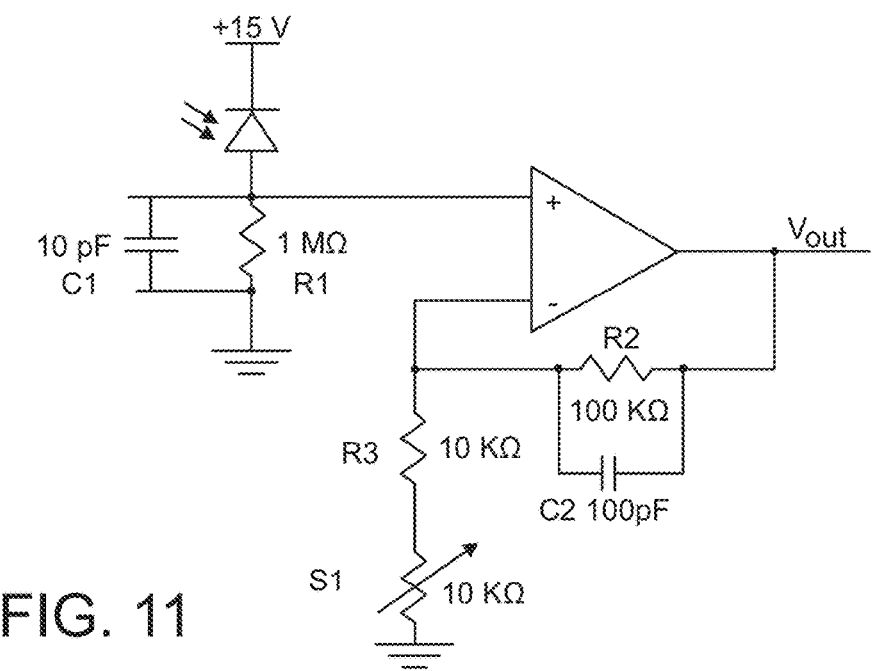
FIG. 11
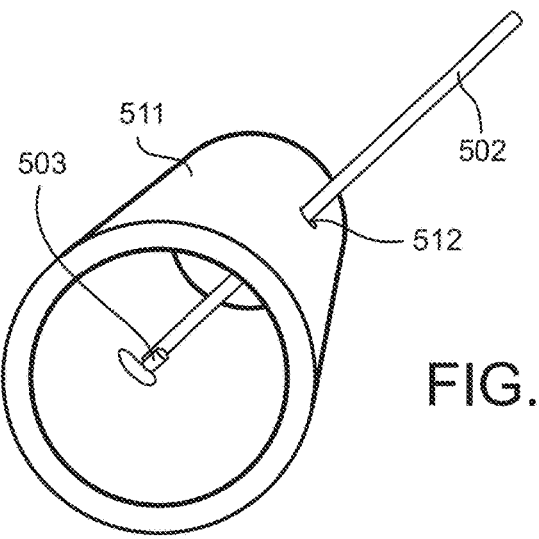
FIG. 12
FIG. 13
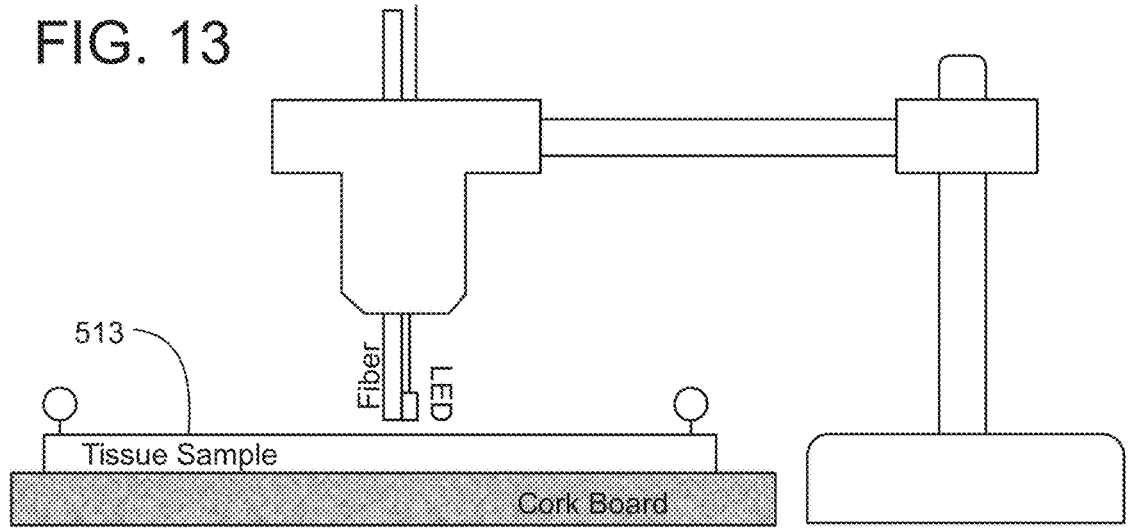

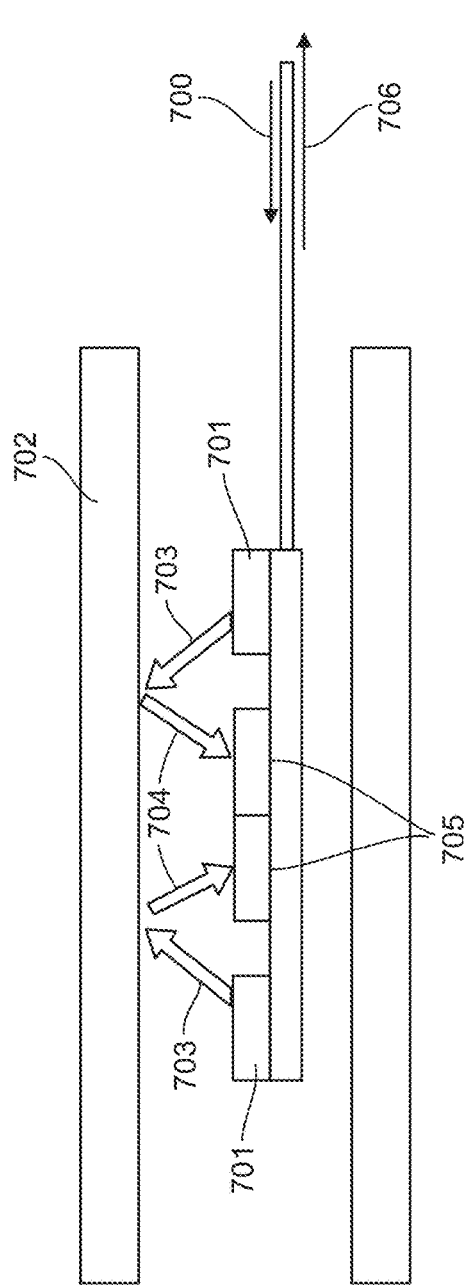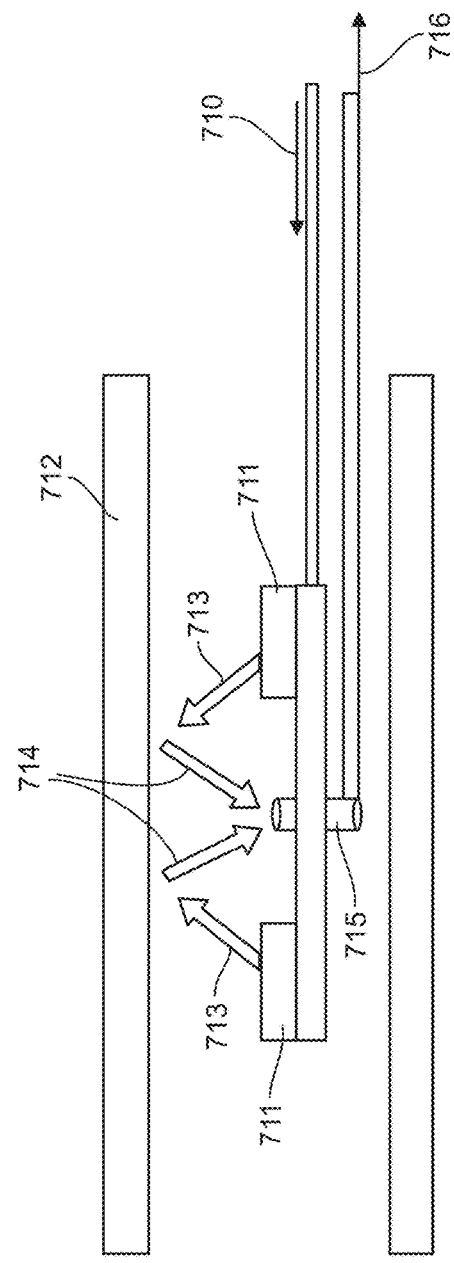
FIG. 16A
FIG. 16B

AIRWAY MANAGEMENT DEVICE FOR IDENTIFICATION OF TRACHEAL AND/OR ESOPHAGEAL TISSUE

CROSS REFERENCE TO RELATED APPLICATIONS

The present application claims the benefit of priority of Patent Cooperation Treaty international patent application number PCT Application No. PCT/US17/16174 filed on Feb. 2, 2017 and U.S. provisional patent application Ser. No. 62/292,277 filed on Feb. 6, 2016, both of which are expressly incorporated by reference herein.

STATEMENT OF GOVERNMENT INTEREST

The invention described herein may be manufactured, used and licensed by or for the United States Government.

BACKGROUND OF THE INVENTION

The invention relates in general to respiratory medical devices and in particular to airway management devices.

Endotracheal intubation (ETI) is a frequent life-saving medical procedure. ETI is often performed in a prehospital or emergency medicine environment when a patient cannot sufficiently breathe of their own accord. Common medical emergencies such as cardiac arrest or trauma often necessitate paramedics or nurses to perform ETI in a chaotic prehospital setting. According to the 2010 Advanced Cardiac Life Support guidelines, a confirmatory procedure should be performed after every ETI to ensure tracheal placement. Failed intubations can lead to death through hypoxemia or through unrecognized intubation of the esophagus.

Even successful intubations, if delayed or performed poorly, can still encounter major adverse events, such as cardiac arrest, hypotension, hypoxemia or asphyxiation due to patient aspiration. Furthermore, multiple attempts at endotracheal intubation has been shown to significantly increase the probability of these adverse events, jumping from 14.2% on first attempt success to 47.2% on the second attempt, to 63.6% chance of adverse events if three attempts were made. In addition to the number of attempts, the time to intubation also adds risk to patient outcomes with longer intubation times leading to extended oxygen deprivation, which has been associated with worse long-term outcomes for traumatic brain injury patients. Currently, confirmation of tracheal tube placement in the clinical field is determined by a variety of mechanisms and approaches, from physical examination to ultrasonographic and impedance-based technologies.

While visualization of the endotracheal tube passing through the vocal cords is considered the "gold standard" of intubation confirmation, visual depth into the patient's upper airway can be severely limited due to their clinical condition or innate anatomical characteristics. These challenges, such as large or swollen tongue, short neck, prominent teeth, or maxillofacial trauma, are categorized as a "difficult airway" and pose problems for standard intubation and visual confirmation techniques. For non-visual methods, tracheal placement can be confirmed by end-tidal carbon dioxide monitoring, capnography, or by applying negative pressure with an esophagus detector device (EDD). However, these methods may require the provider to stop care to perform the confirmation or they may require additional specialized equipment that is not always readily available. Furthermore, not all of the current methods, such as the EDD or visualization, provide continuous patient monitoring to ensure proper tracheal tube placement once intubated. Displacement of the tracheal tube can result from patient movement and can easily be overlooked or go undetected amidst the typically chaotic prehospital, ICU and emergency departments and lead to the same serious adverse events.

A need exists for a feedback mechanism to aid providers in performing successful ETI and other airway management procedures in humans and animals.

SUMMARY OF THE INVENTION

One aspect of the invention is an airway management device for a human or animal subject. The device may include an airway tube having a first end for disposal external to the subject and a second end for disposal in a portion of an airway of the subject. A light emitting element and a photo-sensing element may be disposed at the second end of the airway tube. The light emitting element may be configured to transmit light to tissue adjacent to the light emitting element and the photo-sensing element may be configured to receive reflectance spectra from the tissue. The location of the second end of the airway tube in the airway of the subject may be determined from intensities of the reflectance spectra received by the photo-sensing element across a range of wavelengths.

The device may include at least one signal conduit within or adjacent the airway tube. The at least one signal conduit may be integral with or connected to the light emitting element and the photo-sensing element.

The device may include a signal processor connected to the photo-sensing element via the signal conduit for processing the reflectance spectra from the tissue.

The device may include a spectrum analyzer connected to the photo-sensing element via the signal conduit for processing the reflectance spectra from the tissue.

In one embodiment, the light emitting element includes a light source. In another embodiment, a light source is connected to the light emitting element and configured for disposal external to the subject.

The signal conduit may be one of an electrical and optical signal conduit.

The range of wavelengths may be in the visible light spectrum. The range of wavelengths may be from about 500 nanometers to about 590 nanometers. In one embodiment, the range of wavelengths is from about 530 nanometers to about 580 nanometers.

The tissue may be tracheal tissue and, as wavelengths of the reflectance spectra increase, the intensities of the reflectance spectra may include a first minimum reflectance followed by a maximum reflectance followed by a second minimum reflectance.

Another aspect of the invention is a method of positioning an airway management device in an airway of a human or animal subject. The method may include inserting a distal end of an airway management device in the airway of the subject; illuminating tissue around the distal end of the device with visible light; collecting a reflectance spectrum from the tissue; and comparing the reflectance spectrum to a characteristic reflectance spectrum.

The method may include, before the step of inserting, determining the characteristic reflectance spectrum from one or more tissue samples from a second human or animal subject. The characteristic reflectance spectrum may be taken from tracheal tissue samples. The step of comparing may include comparing intensities of the reflectance spectrum to intensities of a characteristic reflectance spectrum having a wavelength range of about 530 nanometers to about 580 nanometers.

A further aspect of the invention is a method of positioning an airway management device in an airway of a human or animal subject. The method may include inserting a distal end of the airway management device in the airway of the subject; illuminating tissue around the distal end of the device with visible light; collecting reflectance intensity of at least one wavelength from the tissue; and comparing the reflectance intensity to a characteristic reflectance intensity.

The method may include, before the step of inserting, determining the characteristic reflectance intensity from one or more tissue samples from a second human or animal subject. The characteristic reflectance intensity may be taken from tracheal tissue samples.

The step of collecting may include collecting reflectance intensity at one or more of 543 nm, 561 nm and 578 nm wavelengths. The step of comparing may include comparing reflectance intensity at one or more of about 543 nm, about 561 nm and about 578 nm wavelengths to characteristic reflectance intensity at one or more of about 543 nm, about 561 nm and about 578 nm wavelengths.

In one embodiment, the step of comparing may include comparing a reflectance intensity ratio of about 561 nm to about 578 nm to a characteristic reflectance intensity ratio of about 561 nm to about 578 nm. The step of comparing may also include comparing a reflectance intensity ratio of about 561 nm to about 543 nm to a characteristic reflectance intensity ratio of about 561 nm to about 543 nm.

Another aspect of the invention is an airway management device for a human or animal subject. The device may include an airway tube having a first end for disposal external to the subject and a second end for disposal in a portion of an airway of the subject. A light emitting element and a photo-sensing element may be disposed at the second end of the airway tube. The light emitting element may be configured to transmit light to tissue adjacent to the light emitting element and the photo-sensing element may be configured to receive reflectance intensity from the tissue. The location of the second end of the airway tube in the airway of the subject may be determined from the reflectance intensity received by the photo-sensing element at at least one wavelength.

The device may include at least one signal conduit within or adjacent the airway tube. The at least one signal conduit may be integral with or connected to the light emitting element and the photo-sensing element.

The device may include a signal processor connected to the photo-sensing element via the signal conduit for processing the reflectance intensity from the tissue.

In one embodiment, the light emitting element includes a light source. In another embodiment, a light source is connected to the light emitting element and configured for disposal external to the subject.

The signal conduit may be one of an electrical and optical signal conduit.

The at least one wavelength may include one or more of about 543 nm, about 561 nm and about 578 nm wavelengths.

The tissue may be tracheal tissue.

The invention will be better understood, and further objects, features and advantages of the invention will become more apparent from the following description, taken in conjunction with the accompanying drawings.

BRIEF DESCRIPTION OF THE DRAWINGS

In the drawings, which are not necessarily to scale, like or corresponding parts are denoted by like or corresponding reference numerals.

FIGS. 8A and 8B show examples of the smoothed spectra with the minima and maxima circled for both the esophagus (FIG. 8A) and the trachea (FIG. 8B).

FIG. 11 is a schematic of a receiver circuit used to convert photocurrent to voltage and to amplify the signal.

FIG. 12 is a schematic of an "intact" configuration for capturing tracheal tissue reflectance.

FIG. 13 is a schematic of a "mounted" configuration for capturing tracheal tissue reflectance.

FIG. 16A is a schematic diagram of another embodiment of a "front-end" filtering apparatus for an airway management device.

FIG. 16B is a schematic diagram of an embodiment of a "back-end" filtering apparatus for an airway management device.

DETAILED DESCRIPTION

A novel airway management device may be used on subjects such as humans and animals. The device includes an airway tube with a first end that is disposed external to the subject and a second end that is disposed in a portion of the subject's airway. The device may take many forms, for example, the device may be in the form of a bougie, tracheal tube, tracheostomy tube, laryngeal mask, or supraglottic airway devices.

In one embodiment, the device may be used to positively identify tracheal tissue in the subject. In another embodiment, the device may be used to positively identify esophageal tissue in the subject. In a further embodiment, the device may be used to identify one or both of tracheal tissue and esophageal tissue in the subject. The identification of tracheal and/or esophageal tissue may be based on the optical reflectance spectrum of the particular tissue. In one embodiment, the optical reflectance spectrum is in the visible light range.

Figure 1A:
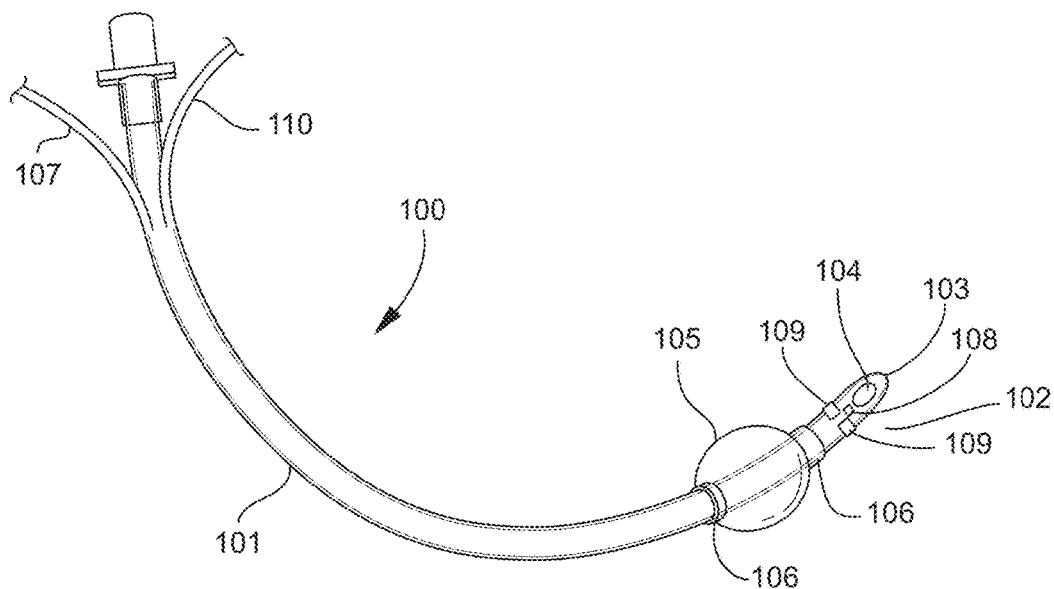
FIG. 1A shows one embodiment of an airway management device.

FIG. 1A shows one embodiment of an airway management device in the form of an endotracheal apparatus 100. Apparatus 100 may include a flexible plastic airway tube 101 having a distal end 102. Distal end 102 may include a bevel tip 103 and a Murphy eye 104. An inflatable balloon cuff 105 may be located near the distal end 102 and fastened to the tube 101 by a pair of sleeves 106. Balloon cuff 105 may be inflated through a lumen 107 running along tube 101.

One or more light emitting element(s) 108 and one or more photo-sensing element(s) 109 may be disposed below the balloon cuff 105. Element(s) 108 and 109 may both face outwardly away from airway tube 101. Element(s) 108 and 109 may include signal conduits or may be connected to a signal conduit, such as one or more electrical or optical conduit(s) 110. Conduit(s) 110 may run along (within or external to) tube 101 to an external excitation means (not shown) and/or signal detection means (not shown). The external excitation means may be used for user notification.

Figure 2:
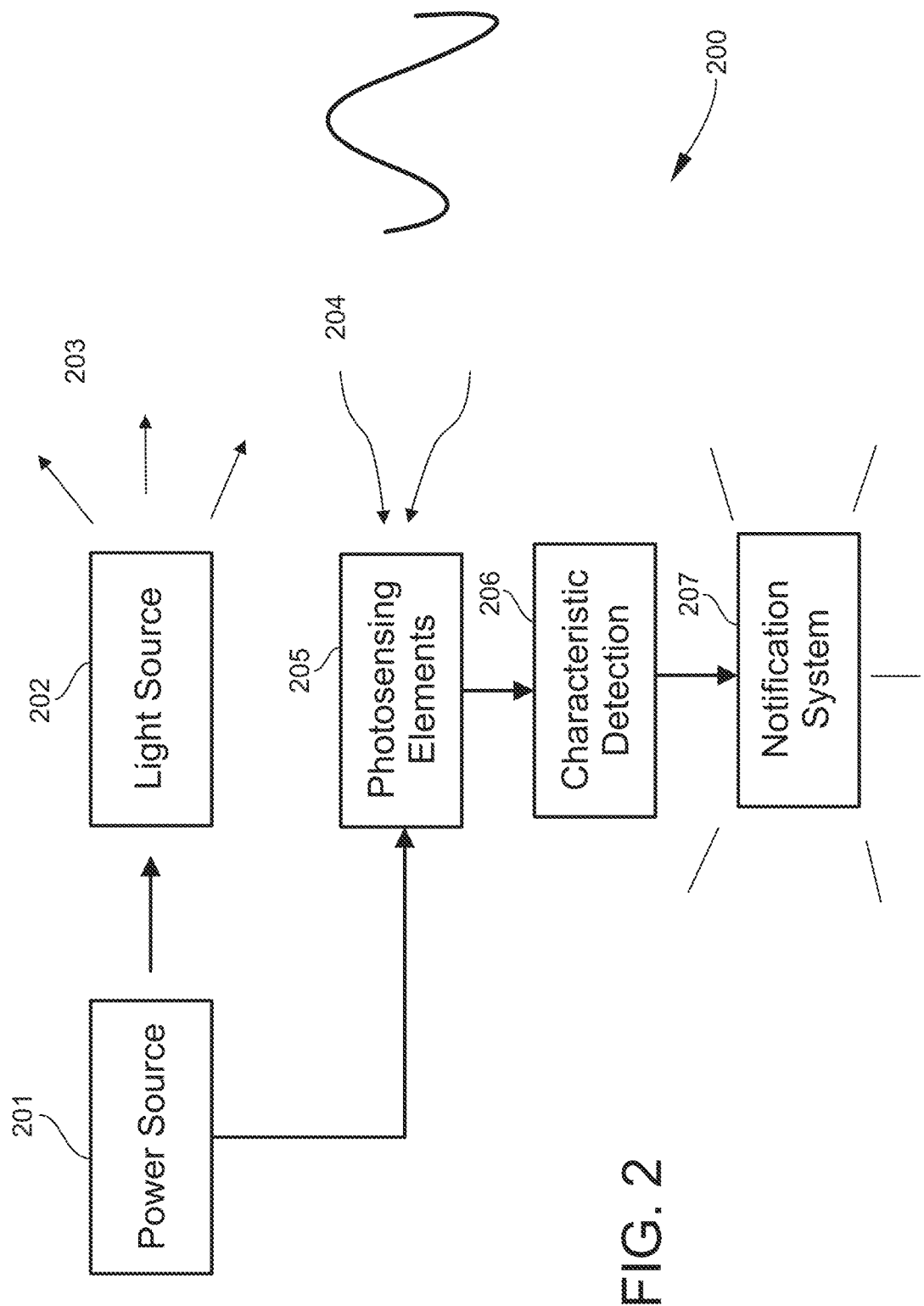
FIG. 2 is a block diagram of electrical and optical components of the embodiment of FIG. 1A.

FIG. 2 is a block diagram of one embodiment of a tissue detection system 200 for use with, for example, the apparatus 100 of FIG. 1A. A power source 201 delivers power to the light emitting element(s) 202 (108 in FIG. 1A) and/or the photo-sensing element(s) 205 (109 in FIG. 1A). The light emitting element(s) 202 projects light 203 toward the tissue adjacent to the element 202. The tissue may be, for example, esophageal tissue or tracheal tissue. The light 203 then reflects off the tissue with a reflectance spectrum 204 that is characteristic of the biological tissue. The reflectance spectrum 204 is captured by the photo-sensing element(s) 205 (109 in FIG. 1A).

The photo-sensing elements 205 may include filtering to capture the key characteristics of the spectrum 204. The output of the photo-sensing elements 205 may be compared at block 206 with the characteristics of a known reflectance spectrum. A known reflectance spectrum, such as in FIG. 4, may be obtained beforehand from tissues samples, such as tracheal tissue samples or esophageal tissue samples. The output from the characteristic detection block 206 may be used to detect the desired tissue and may be as basic as, for example, a binary value of "1" or "0" corresponding to "detection of the trachea" or "no detection of the trachea". Or, the output from the characteristic detection block 206 may be, for example, a binary value of "1" or "0" corresponding to "detection of the esophagus" or "no detection of the esophagus."

The binary signal may be transferred to a notification system 207 to notify the user that the distal end 102 of the airway tube 101 is in, for example, the trachea or the esophagus. The notification system 207 may include, for example, one or more lights or sounds.

Figure 1B:
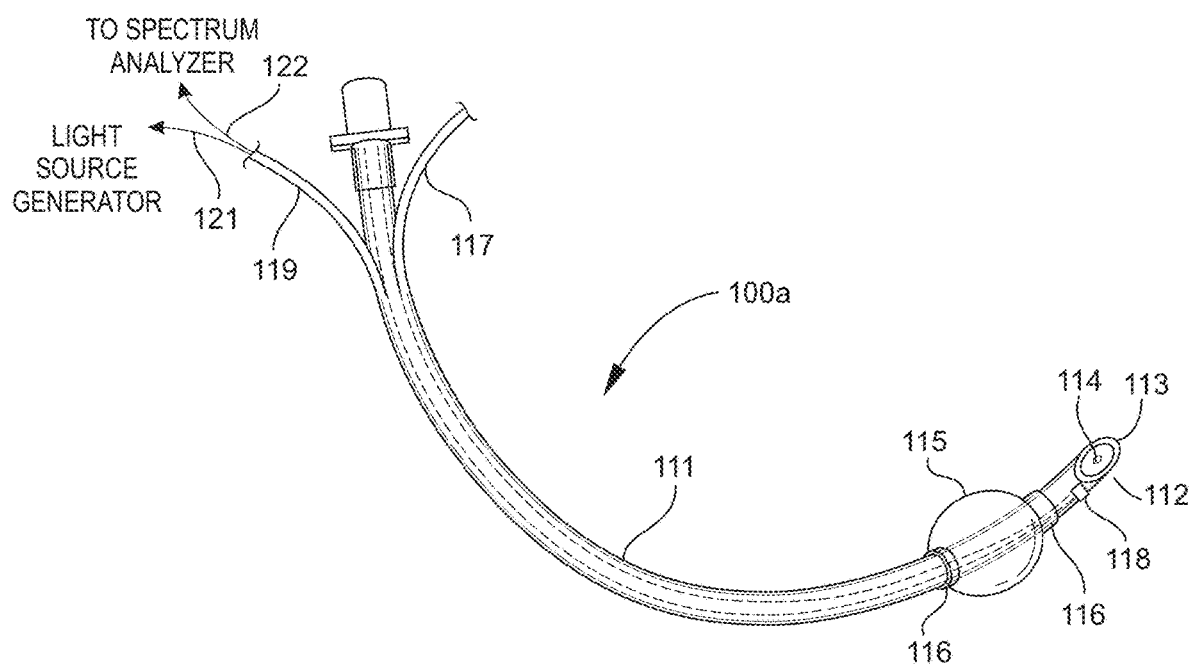
FIG. 1B shows another embodiment of an airway management device.

FIG. 1B shows another embodiment of an airway management device in the form of an endotracheal apparatus 100a. Apparatus 100a may include a flexible plastic airway tube 111. Tube 111 may have a distal end 112 with a bevel tip 113 and Murphy eye 114. An inflatable balloon cuff 115 may be located near the distal end 112 and fastened to the tube 111 by a pair of sleeves 116. Cuff 115 may be inflated through a lumen 117 running along tube 111. One or more fiber probe(s) 118 may be disposed below the balloon cuff 115. Probe(s) 118 may be mounted along or within the flexible tubing 111 itself. Fiber probe(s) 118 may emit light and may collect or receive the reflectance spectrum captured from the light reflecting off the surrounding tissue wall. Fiber probe 118 may be connected to one or more signal conduit(s) 119. Signal conduit(s) 119 may be disposed within or mounted alongside tube 111. Conduit(s) 119 may bifurcate into portions 121 and 122, or, in the case of multiple conduits, each may continue to external connections through 121 or 122. Portion 121 may connect to an external light source generator (not shown) and portion 122 may connect to a spectrum analyzer (not shown).

Figure 3:
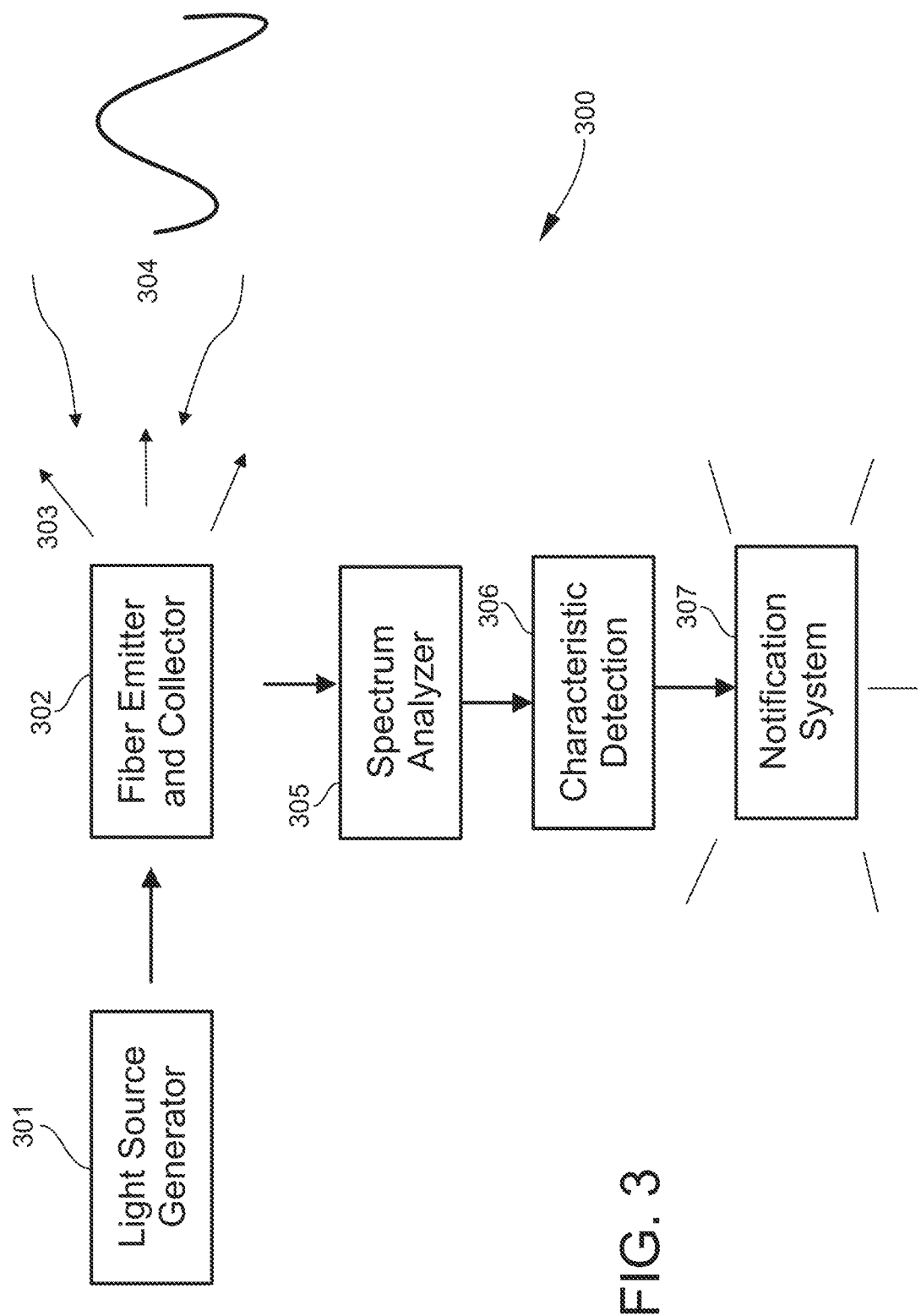
FIG. 3 is a block diagram of electrical and optical components of the embodiment of FIG. 1B.

FIG. 3 is a block diagram of one embodiment of the system circuitry 300 for use with, for example, the apparatus 100a of FIG. 1B. A light source generator 301 may deliver power to the fiber probe(s) 302 (118 in FIG. 1B). The fiber probe(s) 302 may project light 303 toward the surrounding tissue. The light 303 may then be reflected off the tissue with a reflectance spectrum 304 that is characteristic of the biological tissue. The reflectance spectrum 304 may be captured by the fiber probe(s) 302 (118 in FIG. 1B).

The captured spectrum 304 may be passed through and digitized by a spectrum analyzer 305. A characteristic detection algorithm 306 may be used to detect the desired characteristic of the tissue. The characteristic detection algorithm 306 may be created beforehand from known tissues spectra, such as the spectrum in FIG. 4. The output from the characteristic detection algorithm 306 may be as basic as, for example, a binary value of "1" or "0" corresponding to "detection of the trachea" or "no detection of the trachea". Or, the output from the characteristic detection algorithm 306 may be, for example, a binary value of "1" or "0" corresponding to "detection of the esophagus" or "no detection of the esophagus."

The output signal may be transferred to a notification system 307 to notify the user that the distal end 112 of the airway tube 111 is the desired detected tissue, for example, the trachea or the esophagus. The notification system 307 may include, for example, one or more lights or sounds.

Figure 4:
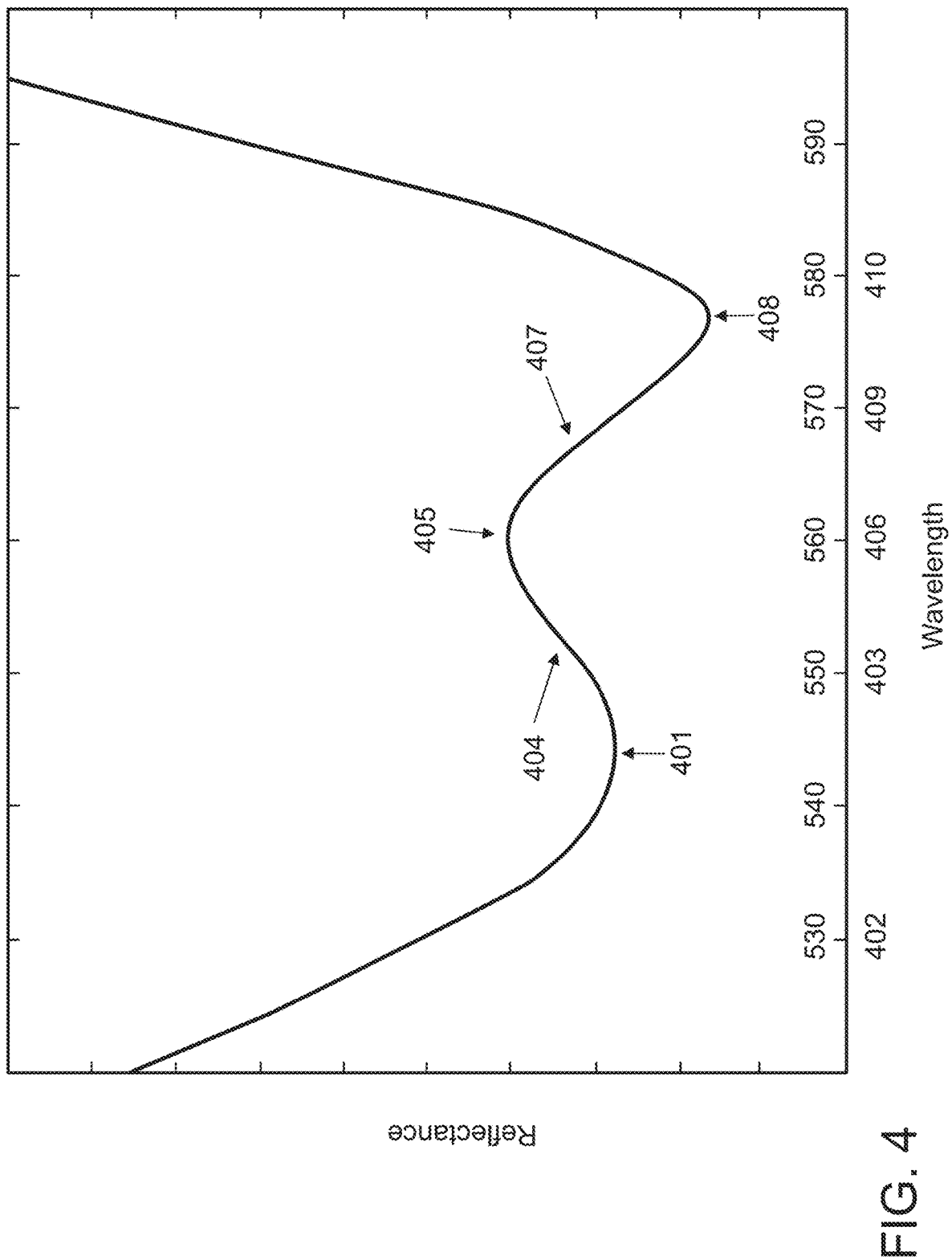
FIG. 4 is a one embodiment of a characteristic reflectance spectrum of a porcine tracheal wall.

FIG. 4 is a one embodiment of a characteristic reflectance spectrum of a porcine tracheal wall. The x-axis is wavelength in nanometers. The y-axis is units of reflectance. A minimum reflectance 401 occurs between a wavelength of approximately 530 nm, denoted at 402, and approximately 550 nm, denoted at 403. A positive slope 404 indicates an increase in reflectance and occurs between the minimum 401 and the peak 405 depicted near a wavelength of approximately 560 nm 406. A negative slope 407 follows the peak 405 showing a decrease in reflectance until a second minimum 408 occurring between a wavelength of approximately 570 nm, denoted at 409, and a wavelength of approximately 580 nm, denoted at 410. The reflectance spectra, such as 204 in FIG. 2 or 304 in FIG. 3, may be compared to the characteristic reflectance spectrum of FIG. 4 to determine if the distal end of the airway device is adjacent to tracheal tissue. A variety of methods may be used to compare spectra 204, 304 with the characteristic reflectance spectrum of FIG. 4.

Figure 5:
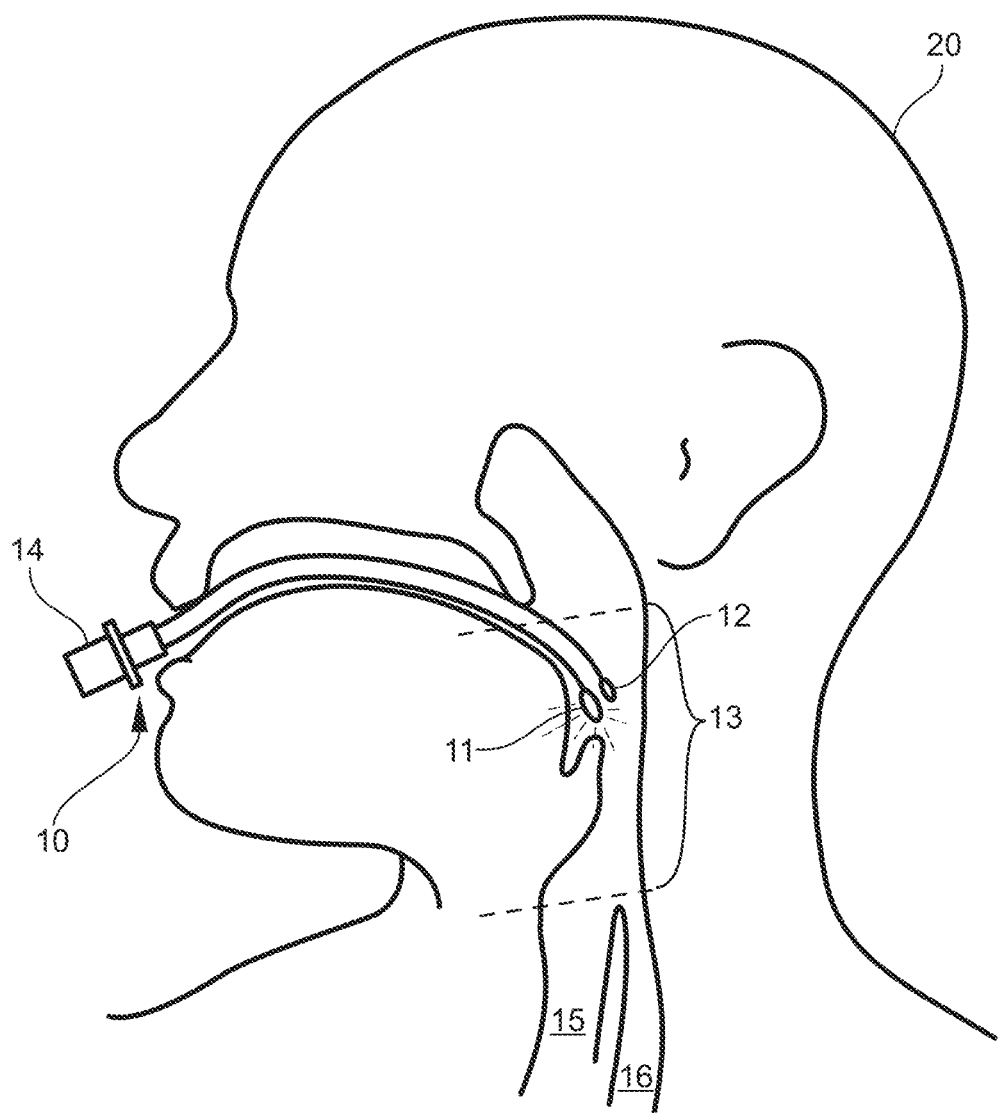
FIG. 5 is a conceptual view of an airway management device in the airway of a human being.

FIG. 5 is a conceptual view of an airway management device 10 in the airway of a human being 20. At the distal end of the device 10 are a light source 11 and an optical detector 12. Below the pharynx region 13 are the trachea 15 and esophagus 16. The device 10 includes a feedback mechanism 14, for example, a light visible to the user or a sound audible to the user. The purpose of FIG. 5 is to show how an airway management device 10 may be oriented in a human 20. Device 10 may include components not shown in FIG. 5.

Research and Testing

Our investigation consisted of two stages: ex vivo and in situ studies. Our initial exploration aimed to investigate the spectral response of tracheal and esophageal tissue samples, excised from pigs, while our continued experiments endeavored to confirm the initial investigations in pig models with more clinically applicable technologies.

Ex Vivo Testing

Tests exploring the spectral properties of tracheal and esophageal tissue were first conducted at the Photonics Research Center (PRC) at the United States Military Academy in West Point, N.Y. using excised porcine tissue samples ordered from Animal-Biotech (Dallas, Tex., USA). Two intact larynx, trachea and esophagus samples were harvested and shipped overnight in a styrofoam cooler stored over ice. All tests were conducted upon receipt within 30 hours of harvesting. Both the trachea and esophagus were dissected from the larynx, separated from each other, and sliced longitudinally to expose the inner tissue lining (lumen). Each tissue sample was then dissected into three horizontal sections to represent the upper, mid and lower portions of the trachea and esophagus, respectively. Additional slices of the epiglottis and vocal folds were also taken from the larynx, the region just above both the separation of the trachea and esophagus. All slices were individually mounted onto cork such that they lay flat for imaging with the hyperspectral camera.

Hyperspectral Camera Instrumentation

Images of the tissue were taken using an OKSI Hyperscan VNIR imager and HyperVision software (Opto-Knowledge Systems, Inc, Torrance, Calif.). Spectral data were collected in a sweep mode, yielding one column of spatial data with the full 520 wavelength elements for each CCD exposure and resulting in a total image spectrum from 396 nm to 1050 nm at each pixel with a 1.25 nm spectral resolution. All samples were illuminated with four white lights (4700K, D50) and one UV LED (396 nm, Edmund Optics, Barrington, N.J.) within a fully-enclosed blackout box to isolate the camera and sample from external light.

To obtain a background noise offset, a dark reference spectrum was collected with all the lights off and the camera shutter closed. A white reference spectrum was also collected by imaging a 99% reflectivity standard (5# White Balance Target, #58-610, Edmund Optics, Barrington, N.J.) exposed to all five lights. Since the data collected from each image represented the intensity of the light collected at each pixel for each wavelength, the following equation was used to convert the data into reflectance:

$$\text{Reflectance} = \frac{\text{signal} - \text{dark}}{\text{white} - \text{dark}} \times 1000.$$

Signal represents the image data collected from the sample, dark represents the calibration image collected with the shutter closed and lights off, and white represents the calibration image data collected from a 100% reflectance standard with the lights on after setting the integration time. The multiplication by 1000 served to normalize the intensity values to a range within which the software could effectively operate.

Ex Vivo Data Analysis

After imaging, the hyperpectral data were processed with the Hypervision software to generate spectral curves for multiple points on each section of the trachea and esophagus along with corresponding color images of the complete imaged section. Each image was randomly sampled at several points to obtain the spectral reflectance curves. Each sampled point consisted of a 10×10 pixel square, with each pixel comprising an approximate 95 µm×95 µm square of the imaged section, resulting in each spectral curve being the average spectral reflectance over an approximately 1 mm$^2$ area on the imaged section.

In Situ Testing

In situ tests were conducted at the United States Army Institute of Surgical Research in Fort Sam Houston, Tex. Pig models were obtained from a previously approved IACUC protocol within the Institute involving a procedure that ended in euthanasia and did not compromise the properties of the upper respiratory system. In order to remain as close as practical to in vivo representation, spectral data were collected from each pig within two minutes of the euthanasia before any post-mortem changes or degradation could affect the local tracheal and esophageal tissue properties.

The endotracheal tube remained in the trachea from the procedure, and the fiber optic probe was passed through the tube into the tracheal region. The tube was then retracted to expose the distal end to the luminal tissue and the reflectance spectrum was displayed in real-time using SpecSoft and captured. The probe was repositioned to capture the reflectance profile from six different locations within the trachea. After saving the tracheal reflectance spectra, the probe was removed from the endotracheal tube and cleaned with an isopropanol surface disinfectant wipe (CaviWipe™, Metrex Research, LLC, Orange, Calif. USA). The probe was then inserted into the esophagus and the reflectance spectrum displayed, captured and stored at three different locations. The endotracheal tube was left in place to ensure that the probe did not re-enter the trachea.

Fiber Optic Instrumentation

For in situ testing, reflectance spectra were captured using a fiber optic reflection probe connected to a compact spectrometer and a halogen white light source. The fiber optic reflection probe connects to the white light source and the compact spectrometer with the distal tip placed in the endotracheal tube. The compact spectrometer is connected to a laptop computer via a USB connection.

The fiber optic probe was a 200 µm core, 200 µm long reflection probe (R200-7-UV-VIS, Ocean Optics, Dunedin, Fla. USA). The compact spectrometer was sensitized for 420 nm to 1070 nm with a 2048×14 pixel Hamamatsu S9840 back-thinned CCD (SPM-002-DT, Photon-Control, Vancouver, BC, Canada) and was connected via USB to a laptop with the matching SpecSoft software. To account for background interference and the imperfections of the white light source, dark and white reference spectra were collected and stored. The dark spectrum was stored with all ambient lights and the white light source off while the probe was covered with black felt. The white light source was then turned on and the distal end of the probe placed in a white integration sphere (FIOS-1, Ocean Optics, Dunedin, Fla. USA) to capture the reference white spectrum. The same reference spectra were loaded before each data collection.

In Situ Data Analysis

The reflectance, absorbance, and amplitude spectra collected through the SpecSoft Software were stored as text files and imported into MATLAB for spectral analysis. Each pig was numerically identified as 1 through 8 and the respective tracheal and esophageal spectra organized accordingly. The tracheal and esophageal spectra were plotted separately and jointly for each pig to isolate as well as compare the unique features. To compare spectra among the pigs, the reflectance spectra for each pig's trachea and esophagus were averaged by summing the value at each data point across the captured profiles and dividing by the number of profiles in order to arrive at one reflectance spectrum representing the trachea and one reflectance spectrum representing the esophagus for each pig. The averaged reflectance spectra were then compared among the pigs by plotting them simultaneously.

To quantitatively characterize and compare the unique features of the spectra, the minimum and maximums within the region of interest (530 nm to 580 nm) were determined for each spectrum. The spectra were first smoothed by applying a 10-window moving average filter. The mean and standard deviation of the wavelength occurrence of the maximums and minimums was determined for each pig. The relative amplitudes, wavelength distances and slopes were calculated between each maximum and minimum for each spectrum and averaged for one mean per pig.

Results

Ex Vivo Results

Figure 6A:
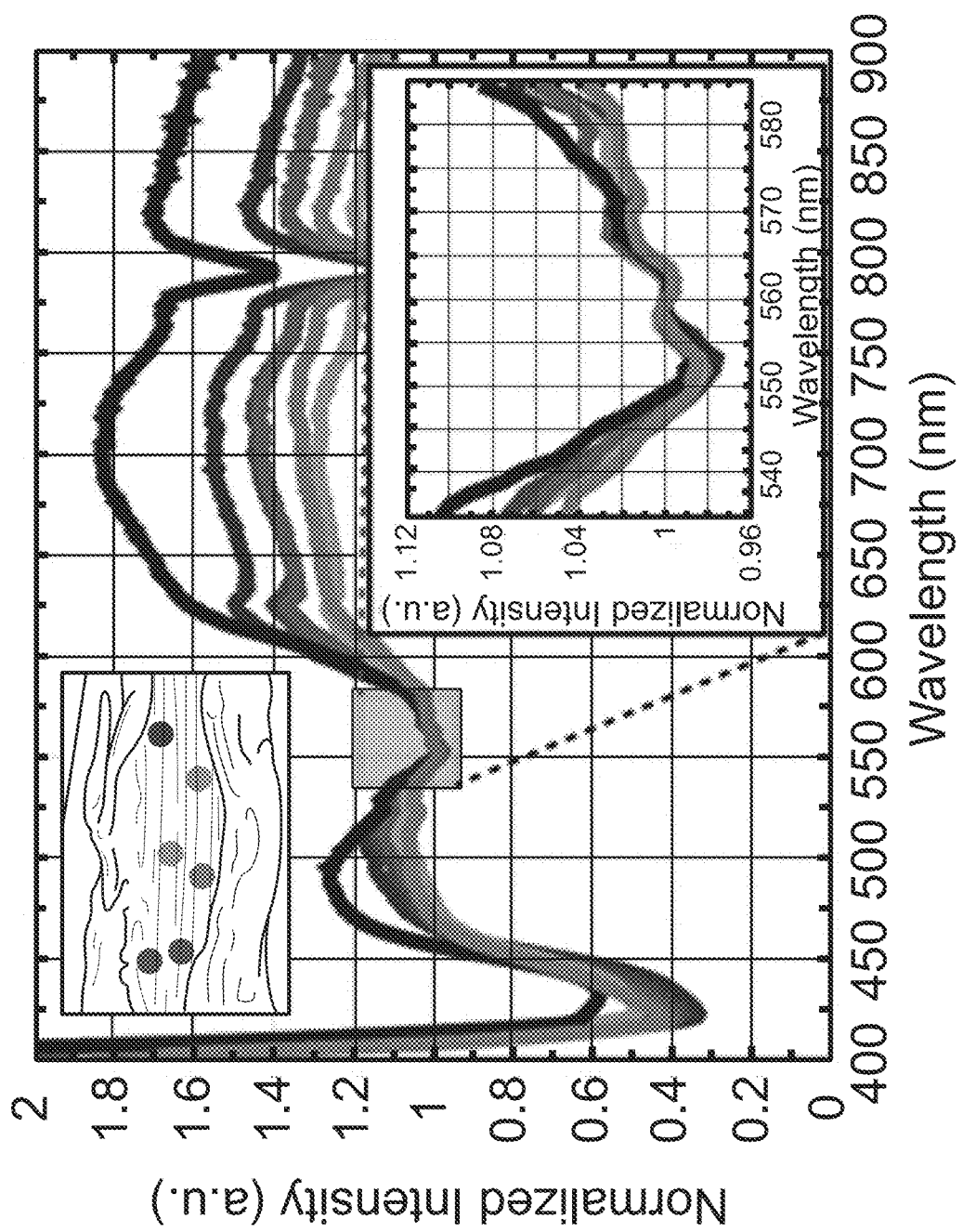
FIGS. 6A and 6B show normalized representative samples of the spectral curves found for a porcine esophagus (FIG. 6A) and a porcine trachea (FIG. 6B).
Figure 6B:
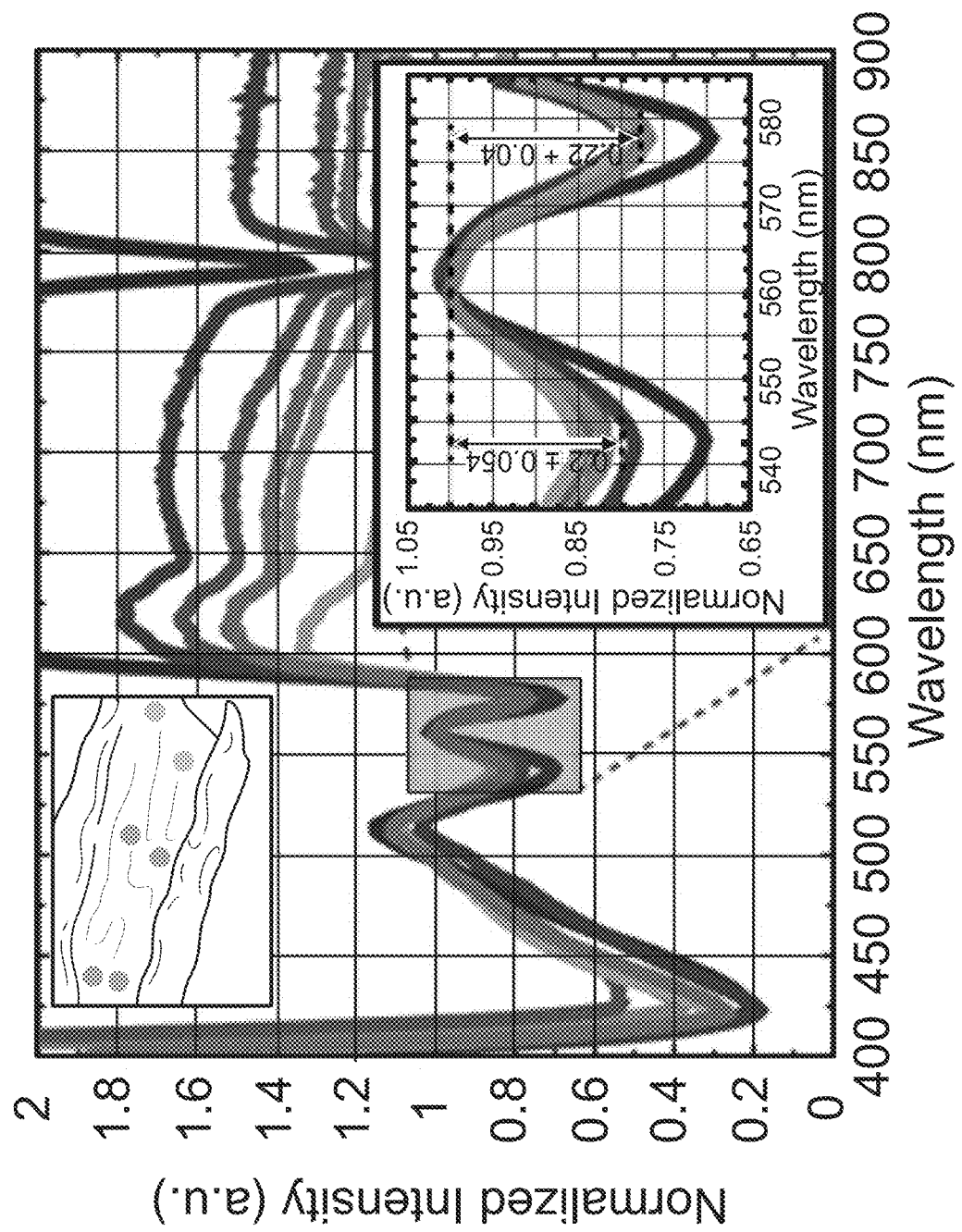

Over 200 distinct points were sampled across the two tracheal and esophageal samples. Qualitative examination of the spectral curves from the samples showed no difference among the different sections (upper, middle, and lower) within each respective tissue type; however, the spectral curves of the tracheal tissue compared to the esophageal did show a significant difference in the profiles as seen in FIGS. 6A and 6B. FIGS. 6A and 6B show normalized representative samples of the spectral curves found for both the esophagus (FIG. 6A) and the trachea (FIG. 6B). The key spectral difference is a distinct peak followed by two local minima seen in the trachea between 530 nm-580 nm wherein lies a peak at approximately 560 nm and the minimum lie near 540 nm and 570 nm. With the peak qualitatively observed, the data were then normalized to the reflected intensity at the peak (560.9 nm) to both assist in evaluating the peaks qualitatively and determine the strength of the local peak to the relative minima. The insets in FIGS. 6A and 6B show the spectral curve around the peak (535 nm-585 nm), clearly showing the distinctive peak seen in the tracheal tissue that is not present in the esophageal tissue.

FIG. 6A shows reflectance spectra for multiple samples of the porcine esophageal tissue. The inset shows reflectance spectra over the area of interest (535 nm-585 nm) for the esophageal tissue. The image in the upper left corner is taken from the hyperspectral camera with the sample points highlighted by the circles. FIG. 6B shows reflectance spectra for multiple samples of the tracheal tissue. The inset shows reflectance spectra over the area of interest (535 nm-585 nm) for the tracheal tissue. The image in the upper left corner is taken from the hyperspectral camera with the sample points highlighted by the circles.

In order to further characterize the results, the peak and trough locations were compared among upper, middle, and lower sections, between the tissue types and between the two pigs. For the first pig, the location of the peaks and troughs were compared between the top and center sections to determine if the location in the trachea had any difference in the spectral characteristics. An independent t-test was conducted on both samples for the two local minima and the local peak. For the top section, the peak was located at 560.9 nm for both sections, resulting in a p-value of 1, showing no statistical difference. The p-values for the two minima of 0.65 and 0.32 also showed no significant difference. Given the lack of significant difference and no known anatomical or physiological differences that would cause the sections to have different spectral responses, the spectral responses from the different points of each section were combined for the trachea and esophagus, respectively. For the trachea, the averaging of the spectral curves across the points and sections resulted in a peak location of 560.9 nm±1.109 nm and local minima locations of 543.242 nm±0.828 nm and 577.917±0.506 for pig one, and 560.377 nm±1.217 nm and local minima locations of 542.398 nm±0.746 nm and 577.082±0.579 for pig two. Overall, the spectral shape of the "tracheal peak" was the primary characteristic that allowed us to distinguish between the trachea and esophagus subjectively, and was enough of a basis to continue research in situ.

In Situ Results

Figure 7A:
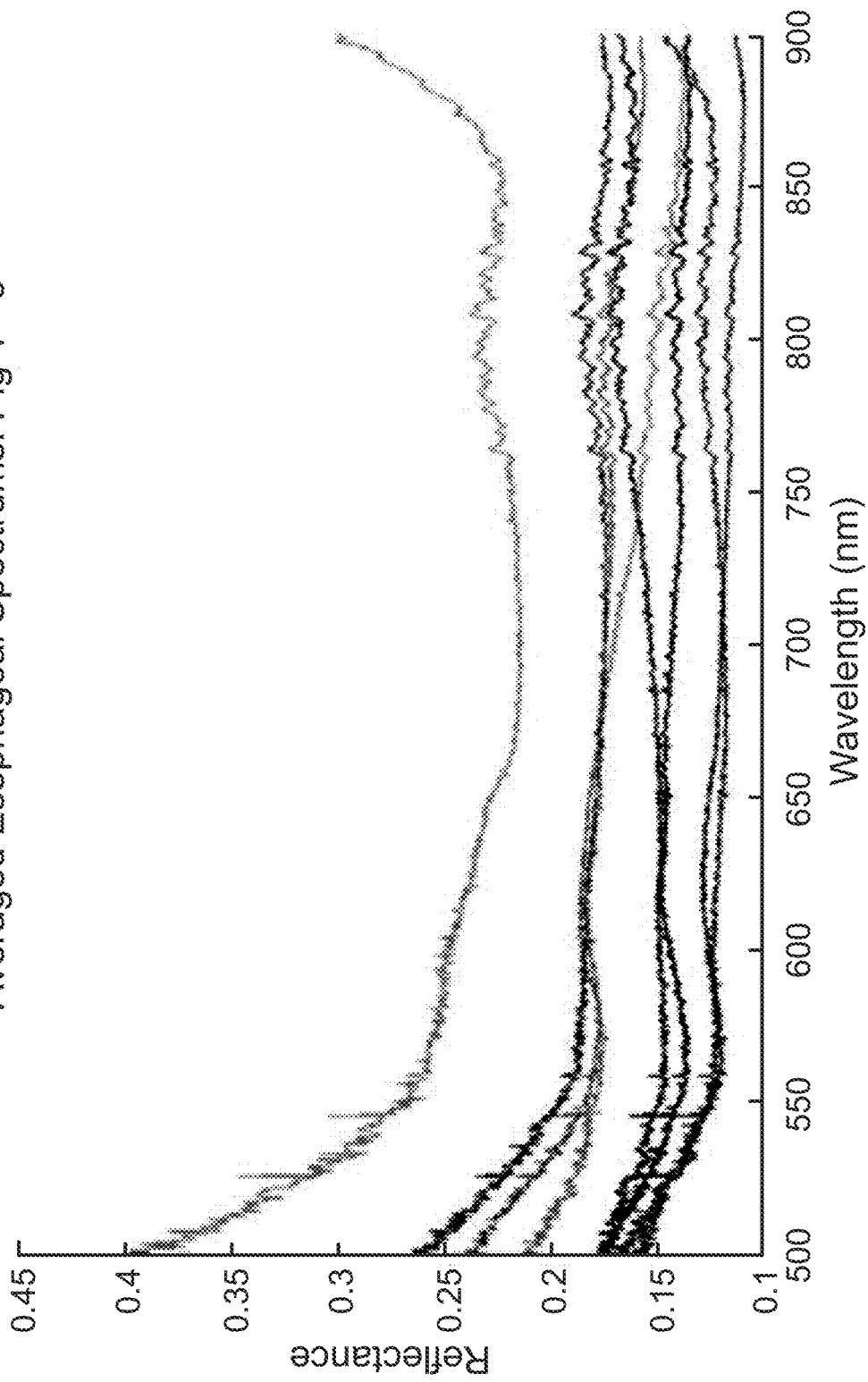
FIGS. 7A and 7B show averaged porcine esophageal spectra (FIG. 7A) and averaged tracheal spectra (FIG. 7B).
Figure 7B:
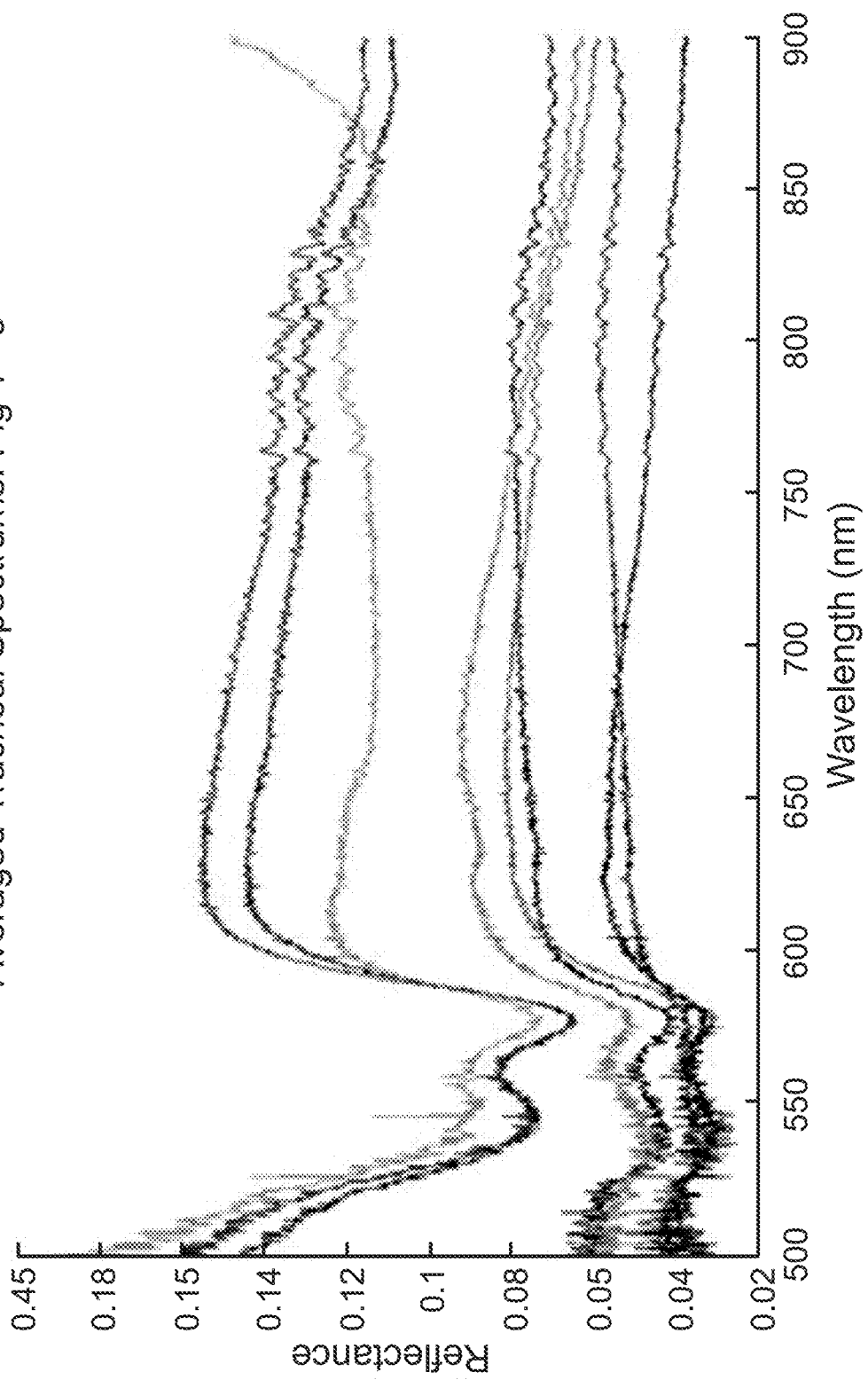

Spectral data were collected on eight pigs, with three to nine spectral captures in both the trachea and esophagus for each pig. In order to collect the data as close to time of death as possible, the same calibration spectrum was loaded in SpecSoft before each test. FIGS. 7A and 7B show the averaged esophageal and tracheal spectra for all the pigs, respectively. There is one spectrum per pig in each of FIGS. 7A and 7B. Initial qualitative analysis confirmed the existence of the "tracheal peak" within the same features as identified by the previous ex vivo investigation, with two minima and a maximum within the region of 530 nm to 580 nm. Conversely, the esophageal spectrum exhibits a more gradual negative slope over the region with no real distinct features across the spectrum.

Figure 8A:
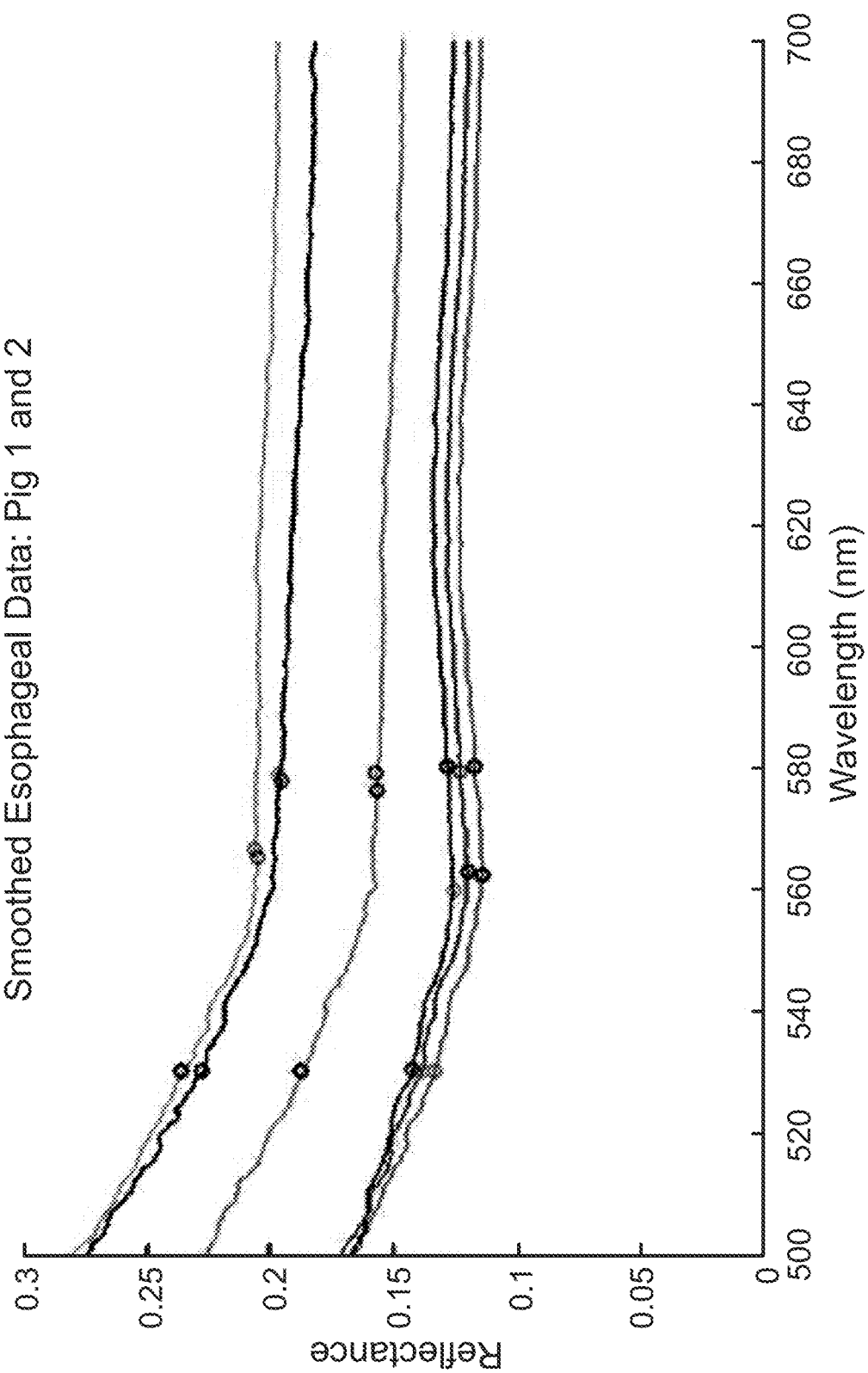

To focus in on the region of interest, 530 nm to 580 nm, we smoothed the data in MATLAB using a moving average filter and created a minima and maxima detection algorithm. FIGS. 8A and 8B show examples of the smoothed spectra with the minima and maxima circled for both the trachea and esophagus. While the minima and maxima algorithm was technically able to extract values for the esophageal spectra (FIG. 8A), the data points were indicative of a gradual negative slope over the region of interest. The first maximum occurred at the beginning of the region 531.35 nm±1.20 nm and the minimum occurred toward the end of the region at 571 nm±5.56 nm. A second maximum was identified at 578.5 nm±1.8 nm; however, 13% of the esophageal spectra captured did not exhibit a second maximum. On the other hand, the tracheal spectra (FIG. 8B) exhibited a clear and consistent pattern of a minimum, maximum, and second minimum for every spectrum. Passing the tracheal spectral data through the minima and maxima algorithm, the minima and maxima were detectible for every spectrum. The first minimum occurred at 541.25 nm±4.84 nm, the maximum occurred at 559.89 nm±1.42 nm, and the second minimum occurred at 576 nm±0.83 nm.

Discussion

The present studies began for the purpose of exploring the possibility of differences in the spectral responses of tracheal versus esophageal tissues. With the primary motivation stemming from finding a more reliable and readily accessible method of tracheal confirmation during intubations in emergency medicine, we endeavored to explore techniques that could be employed in the prehospital environment.

To first look for and capture any unique spectral properties with high resolution, our study began with ex vivo investigations of the tissue responses when exposed to white light using a hyperspectral camera. The ex vivo studies exposed a novel difference in reflectance spectra between the two tissue types, as seen qualitatively in FIGS. 6A and 6B. In particular, the distinct peak that occurred between 530 nm and 580 nm in the tracheal reflectance spectrum was dramatically unique from the esophageal reflectance spectrum across the same region which exhibited a steady decline.

Continuing the investigation, we aimed to explore the potential detectability of this "tracheal peak" using more portable technologies and with the tissue in its natural structure. Using a fiber optic sensor in situ still captured the same unique spectral characteristic of the tracheal peak occurring between the same 530 nm and 580 nm region of interest. The detection of maxima and minima for both tissues highlighted the consistent pattern of a significant positive slope followed by a significant negative slope in the tracheal tissue in contrast to the simpler profile of esophageal tissue which showed a gradual, negative slope over the same range. Corroborating the ex vivo findings, the in situ results supported the consistency of the tracheal peak around 560 nm with the data showing 559.89 nm±1.42 nm. In addition, the minimum following the peak exhibited equivalent reliability in its occurrence at 576 nm±0.83 nm. While the mean wavelength occurrence of the maximums in the esophagus showed low standard deviations as well, 531.35 nm±1.20 and 578.5 nm±1.8, the mean values note that these occur at the edges of the region of interest. Therefore, this result is attributed more to the overall gradual negative slope of the esophageal spectrum rather than indicative of a distinct characteristic that could be exploited for detection purposes.

Comparing the slope characteristics of the tracheal spectra to that of the esophageal spectra, the esophageal data exhibit a steady negative slope with no distinct features between 530 nm and 580 nm while the tracheal spectra show a unique positive slope up to the peak around 560 nm followed by a negative slope to a predictable minimum around 576 nm. These significant differences confirm the hypothesis that there are distinct characteristics of the tracheal tissue versus esophageal tissue that can be detected using clinically practical technologies.

A major limitation of the study involved the decision to use the same previously captured calibration spectrum as the references for each test. Ideally, the dark and white reference would be recalibrated before each testing procedure to account for light source or sensor degradation. However, this decision was made in order to keep the time between time of death and data collection as short as possible to reflect as close to in vivo as practicable. The consequences became apparent with the pigs collected toward the end which resulted in noisier spectra and decreased amplitudes and slopes. Given the promising overall results from this in situ study demonstrating strong detection capabilities using fiber optic sensors, future studies will continue exploration with portable technologies in vivo and account more for known instrumentation limitations. Additionally, the fiber probe in the present study was a commercial-off-the-shelf (COTS) device that was not designed for this particular application, the aperture for the light emission and collection was perpendicular to that of the face of the tissue. We also endeavor in future studies to explore the potential of angled or beveled probes to collect more reflectance signal from the tracheal and esophageal walls.

Conclusion

Through these ex vivo and in situ studies investigating the spectral properties of tracheal and esophageal tissue, we have identified and characterized a definitive difference in the reflectance spectra when exposed to white light. The defining "tracheal peak" observed between 530 nm and 580 nm exhibited consistent and unique characteristics that could be detected using clinically relevant technologies, such as fiber optic sensors. We conclude that this unique property could be implemented using these technologies in order to pursue a more reliable and readily available method of tracheal confirmation during intubation. Future studies will continue to investigate the detectability in vivo and the applicability toward practical tracheal detection devices leveraging the detection mechanism.

Prototypes

Figure 15:
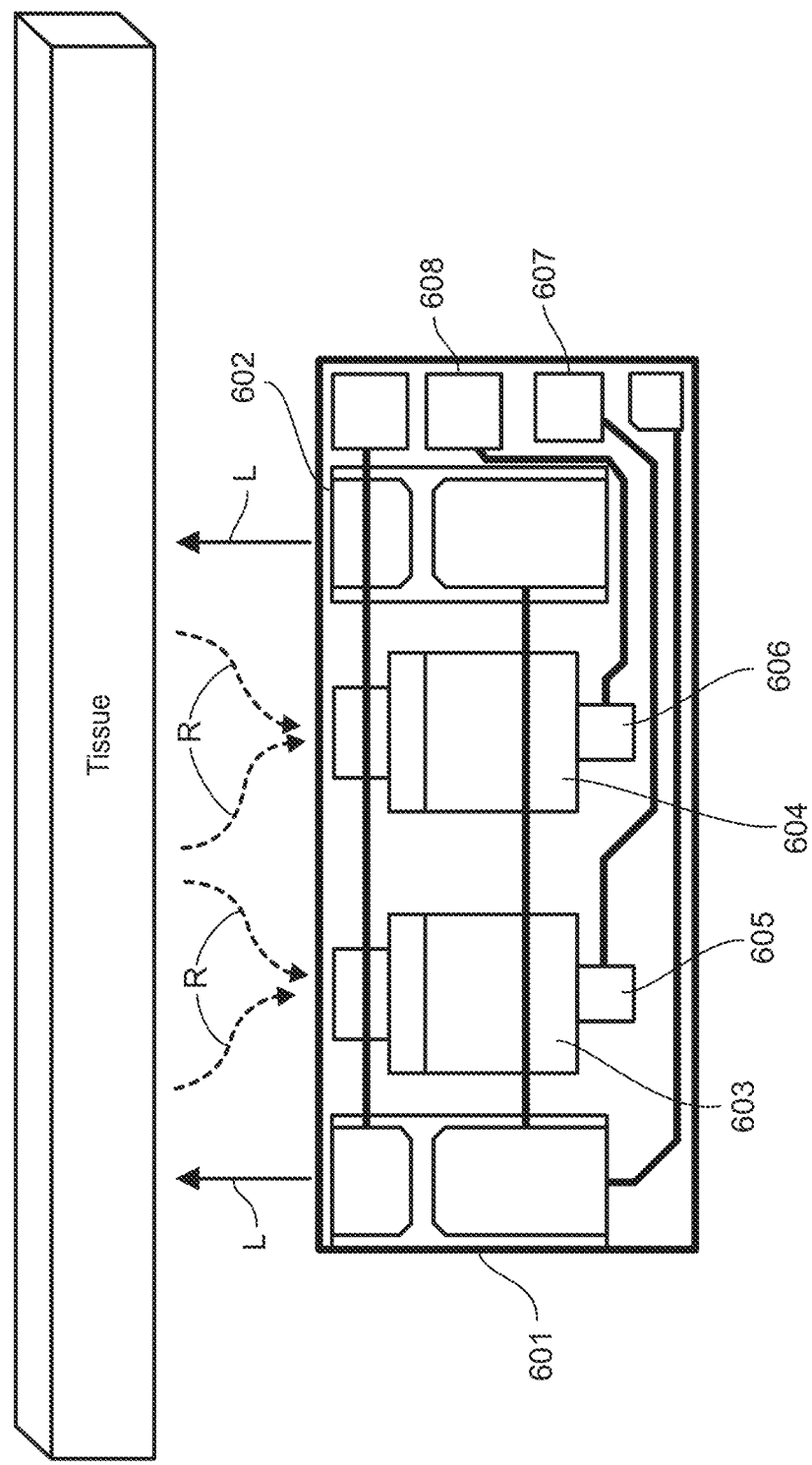
FIG. 15 is a schematic diagram of one embodiment of a "front-end" filtering apparatus for an airway management device.

Two prototypes were fabricated and tested. One prototype or embodiment used "front-end" filtering and the other prototype or embodiment used "back-end" filtering. The "front-end" filtering prototype employs filters at the distal end of the prototype immediately upon capture of the reflected light by the distal photo-sensing elements. The "back-end" filtering prototype captures and transmits all light reflected from the tissue and filters the light farther from the distal end, allowing for larger filtering components and hardware to remain distanced from the sensing tip thereby reducing the size of the instrument introduced into the patient. FIG. 5 shows an exemplary embodiment of the "back-end" prototype which is further described below. FIG. 15 shows an exemplary embodiment of the "front-end" filtering prototype, which is further described below.

The prototypes were based on the working principle of white light illumination, captured reflectance, selective filtering and relative comparison to distinguish between the two types of tissue: tracheal and esophageal. One prototype design relied on a plastic optical fiber probe situated next to a white light emitting diode (LED). In the other prototype design, the photodiodes were placed directly in the tissue next to the LEDs to achieve a greater amount of reflection return. Due to the large size of the glass filters, the prototype with both the LED and the photodiodes at the tissue interface was not tested. The study discussed below focused on the fabrication and testing of the plastic optical fiber probe design.

Detection Logic

The detection logic for the prototype consisted of comparison of the returns from the different regions of the spectra where a significant difference between the tissues was expected. Based upon the previously characterized reflectance curves for the tracheal and esophageal tissue, the most distinct features of the tracheal tissue are the peak seen at approximately 561 nm and the two local minima seen at approximately 543 nm and 578 nm. To test for detection of tracheal tissue, we compared the relative reflectance intensity at 561 nm to that of the relative reflectance intensities at 543 nm and at 578 nm, as described in Equation 1:

$$\Delta R_{561,543} = R_{561} - R_{543} \Delta R_{561,578} = R_{561} - R_{578} \quad \text{Equation 1:}$$

In Equation 1, $R_{561}$, $R_{543}$, and $R_{578}$ are the responses from the photodiode and receiver circuit through the 561 nm, 543 nm, and 578 nm filters, respectively. A positive detection was declared if the response at 561 nm exceeded the responses at 543 nm and at 578 nm beyond a defined threshold T (Equation 2 below), measured to account for resolution of the oscilloscope, any imbalance in balancing of the circuits and noise.

$$T = \sqrt{\text{ScopeResolution}^2 + \text{Noise}^2 + \text{GainDifference}^2} \quad \text{Equation 2:}$$

Figure 9:
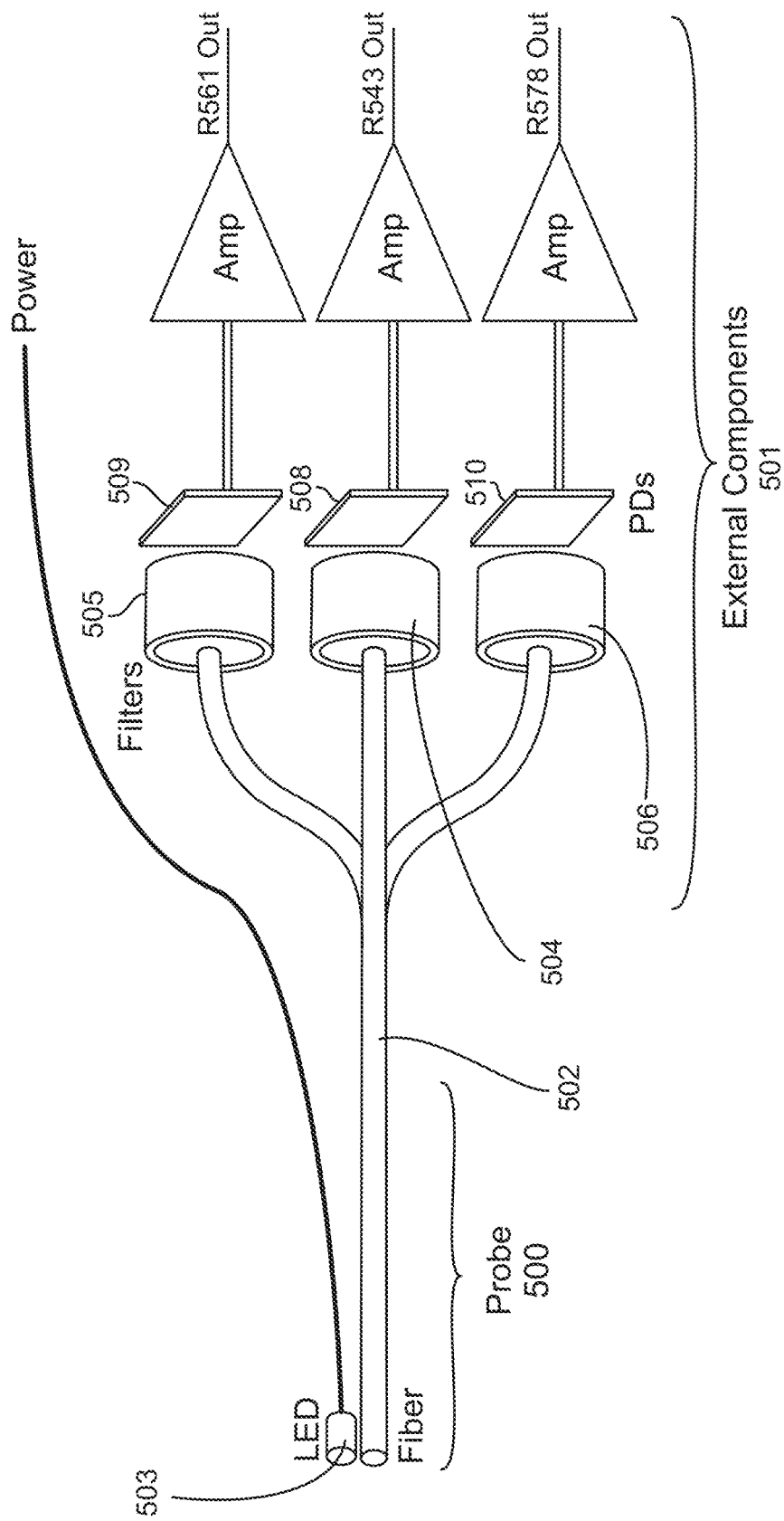
FIG. 9 is a schematic of an embodiment of an airway management device showing a fiber-optic probe and external components that filter and amplify the received reflectance.

This detection logic was chosen for its implementation compatibility through use of inexpensive, discrete integrated circuit components, such as comparators. FIG. 9 is a schematic of a prototype of an airway management device showing the fiber-optic probe 500 and external components 501 to filter and amplify the received reflectance to thereby implement the detection algorithm. For the purpose of raw output observation and data collection in this prototype, the output voltages at the selected wavelengths were recorded manually and the differential magnitudes compared in a spreadsheet computer program rather than using comparator circuits.

Detection logic can also be employed through a ratio comparison between 561 nm and either 543 nm or 578 nm, as shown in Equations 3(a) and 3(b) below:

$$\text{Ratio } B = R_{561}/R_{543} \qquad \text{Equation 3(a):}$$

$$\text{Ratio } Y = R_{561}/R_{578} \qquad \text{Equation 3(b):}$$

Ratio comparison can still be implemented in circuitry hardware using discrete components, such as comparators, or an algorithmic approach programmed into a microcontroller. Detection through ratio comparison helps to overcome the limitation of variable signal intensity based on distance from the tissue or other variables such as the presence of bodily fluids or blood.

"Back-End" Filtering Probe

As shown in FIG. 9, one prototype used a plastic optical fiber (POF) probe 502 coupled with a white light emitting diode 503. Utilizing a fiber probe 502 allows for the majority of the electronics to be positioned outside of the intubation tube, simplifying the design. One of the constraints was the filters to use in the prototype. Some off-the-shelf discrete filters were too large to utilize inside of an intubation tube at the point of measurement. So, for this prototype, the filters and detection electronics were located outside of the intubation tube. The filters 504, 505, 506 chosen were from Edmunds Optics, with a 12.5 mm diameter. Details of the filters 504, 505, 506 are in Table 1 below.

TABLE 1

Specifications of filters used to isolate desired wavelengths

| Filter | Center λ (nm) | Center Tolerance (nm) | Full Width-Half Max (nm) | FWHM Tolerance (nm) |
|---|---|---|---|---|
| Edmunds 65-642 | 540 | 2 | 10 | 2 |
| Edmunds 67-766 | 560 | 3 | 10 | 2 |
| Edmunds 67-768 | 577 | 3 | 10 | 2 |

The probe segment 500 that would extend down or along the intubation tube into the endotracheal/endo-esophageal space consisted of an Industrial Fiber 1×3 POF coupler 502 and a white LED 503. The POF coupler 502 consisted of a standard jacketed 1000 µm core plastic fiber cable and had a splitting ratio of 33:33:33 to each arm. The distal, sending end of the probe was bent to allow for a greater magnitude capture of the reflected returns. Greater magnitude of the reflected returns may also be achieved with lenses or mirroring techniques, although lenses and mirroring techniques were not used in this particular prototype.

Figure 10:
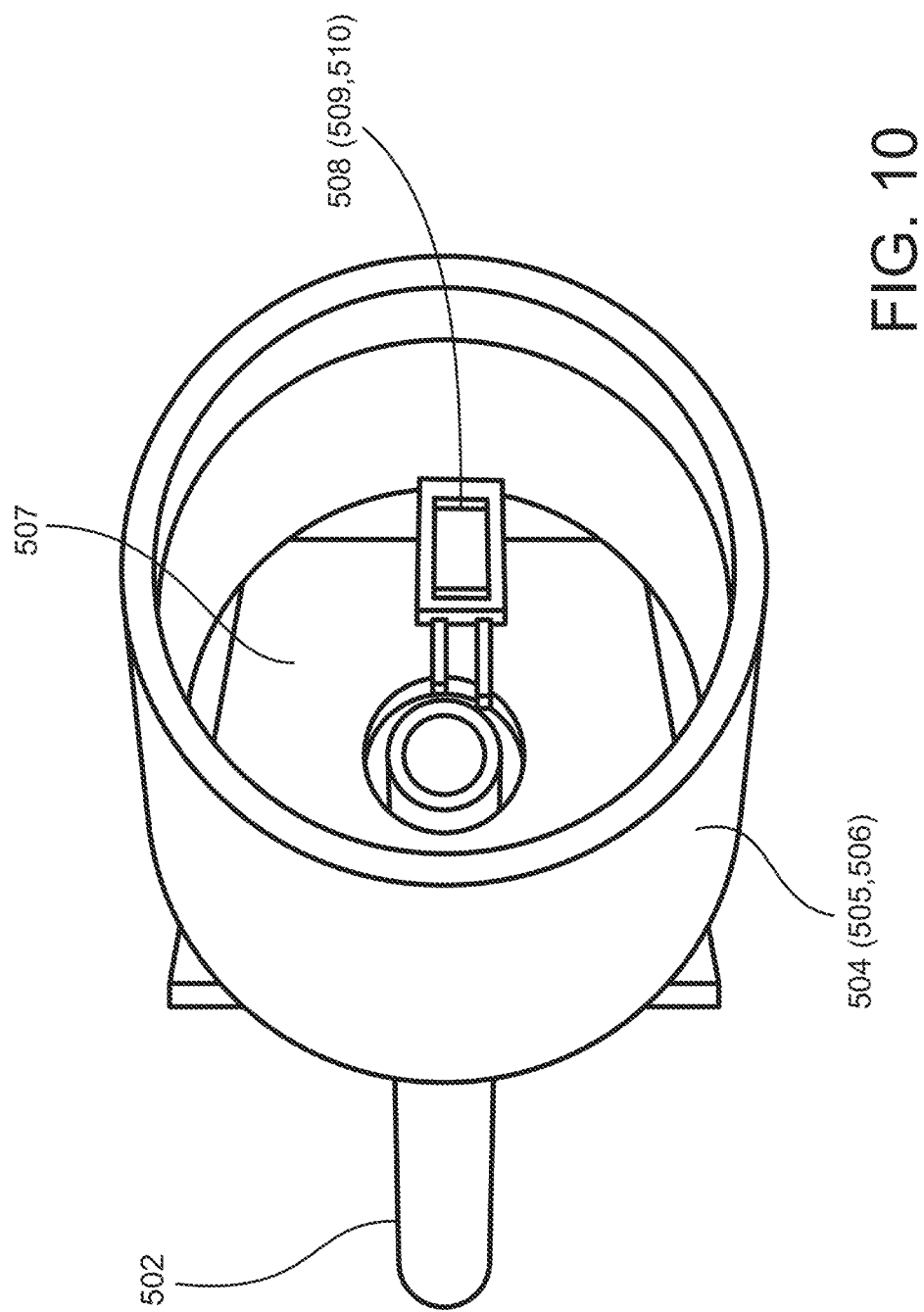
FIG. 10 is a schematic showing the assembly of an optical fiber, filter and photodiode.

FIG. 10 is a schematic showing the assembly of an exemplary filtering apparatus, including an optical fiber, filter and photodiode. The filtering apparatus converts the captured light reflectance into an electrical signal. To attach the fiber returns to respective filters 504, 505, 506, a small square of printed circuit board (PCB) 507 was cut and then drilled in the center with a diameter to match that of the POF 502. The POF 502 was inserted into the hole in the PCB 507, and then cyaoacrylate (CA) was used to secure it. The PCB 507 was then attached to the input of a respective optical filter 504, 505, 506 using CA. Silicon photodiodes (Luna Optoelectronics PDB-C156) 508, 509, 510 were used for detection of the filtered reflected light and were attached to the output side of the optical filters using CA. The normalization procedure (described below) used for the entire system eliminates any issues with the spectral response of CA.

The output of the filtering apparatus of FIG. 10 becomes an electrical signal that is proportional to the intensity of the desired, filtered wavelength. The electrical signal interfaces with the circuitry, discussed below, and is interpreted by the detection logic.

"Front-End Filtering" Probe

Figure 14:
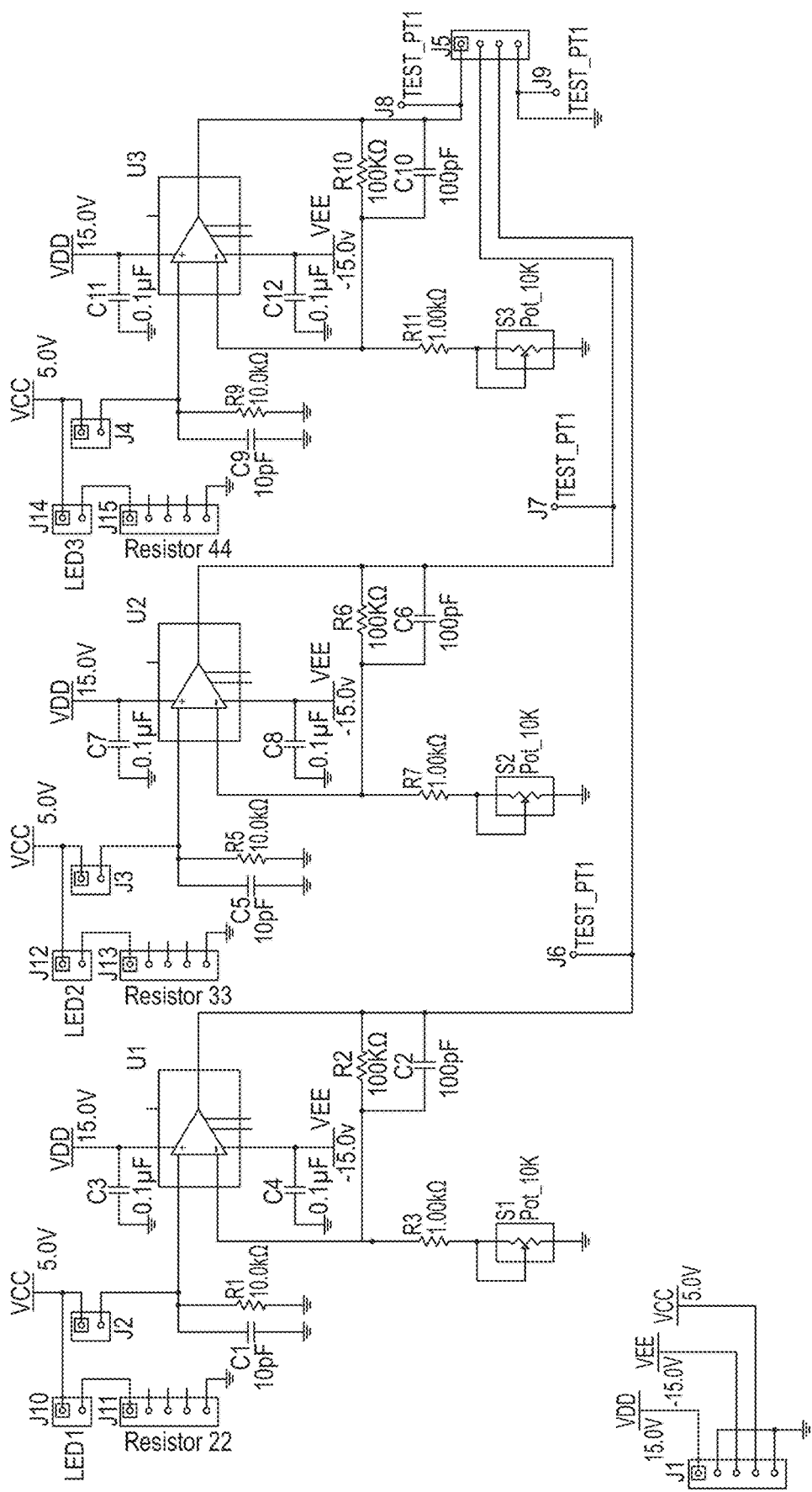
FIG. 14 is a schematic circuit diagram of a printed circuit board having three receiver circuits for an airway management device.

FIG. 15 shows an exemplary embodiment of the "front-end" filtering prototype design where both the illuminating elements 601, 602 are, for example, light-emitting diodes (LEDs) targeted for broadband white light. The receiving elements are glass filters 603, 604 juxtaposed in front of photodiodes 605, 606. The glass filters 603, 604 and photodiodes 605, 606 are disposed on the distal, sensing end of the probe. Glass filters 603, 604 receive and filter the captured light according to the wavelengths of interest. The photodiodes 605, 606 on the backside convert the relative intensity of the filtered light to a voltage that is transmitted to the attached circuitry via wires 607, 608, respectively. In one embodiment, the glass filters 603, 604 target light wavelengths of 561 nm and either 563 nm or 578 nm. The detection logic previously described then compares the reflectance at 561 nm to the reflectance at either or both of 543 nm and 578 nm. In the embodiment of FIG. 15, only two filters 603, 604 and two conduits 607, 608 are used, to thereby minimize the size of the probe. However, in some embodiments, the number of filters and conduits may be more than two so that at least three discrete wavelengths of light can be simultaneously collected and detected. Such an embodiment may require advanced manufacturing capabilities and smaller photodiodes and filters. FIG. 14, discussed below, describes the circuitry that interprets the output from two and/or three output conduits.

In FIG. 15, the solid arrows L extending from the light emitting diodes 601, 602 represent the projected light illuminating the target tissue. The dashed lines R represent the light reflected from the tissue and then captured by the receiving elements and filters.

The Circuitry and Hardware

FIG. 11 is a schematic of a receiver circuit used to convert the photocurrent to voltage and to amplify the signal. FIG. 11 is only one implementation, as there are a multitude of circuits that could be used. The receiver circuit includes a trans-impedance amplifier followed by a single stage non-inverting voltage amplifier. The trans-impedance amplifier includes a 1 MΩ resistor R1 in series with the photodiode. The 10 pF capacitor C1 in parallel with the resistor creates a low pass filter, helping to reduce noise. The trans-impedance amplifier creates a voltage signal out of the photocurrent generated by the reflected light absorbed by the photodiode (part of the probe or separate board depending on implementation). The voltage output of the trans-impedance amplifier is then amplified by a high gain amplifier circuit consisting of a single stage non-inverting operational amplifier circuit. The gain of the circuit is controlled by resistors R2 and R3. S1 is a potentiometer that allows slight adjustment to the gain to normalize the outputs as discussed in following paragraphs. Capacitor C2 is placed across the gain resistor to create a low-pass filter, again to help reduce noise.

FIG. 14 shows the schematic of an exemplary printed circuit board used in testing. The circuit board includes three of the above-described receiver circuits (with resistances changed to modify stage gains) to simultaneously power and interpret the voltage output from both the "back-end" and "front-end" filtering prototypes. In each of the three circuits, the resistance of resistors R2, R6 and R10 may be altered to optimize the signal magnitude collection for the different prototypes. For example, the "front-end" filtering embodiment may use resistors R2, R6 and R10 with a resistance of 100 kOhm and the "back-end" filtering embodiment may use resistors R2, R6 and R10 with a resistance in a range of about 4-7 MOhm.

Calibration Mechanisms

Prior to testing, the amplifier circuits were normalized to account for differences in attenuation losses through the filters, responsivity of the photodiode, and gain in the circuit. The normalization procedure utilized the same 100% white reflectance target as described above to normalize the hyperspectral imaging. The normalization procedure began with dark measurements by placing the probe with the LED turned off in an enclosed black box and recording the output to account for any circuit imbalances and slight differences in photodiode dark current. After recording the dark values, measurements were then taken with the probe aimed at the white reflectance target and the LED turned on, while maintaining the system in the black box. The resulting voltage was then compared to the dark output to get a total difference between white and dark (delta). The gain of each circuit was then adjusted to ensure that all of the circuits had the same delta. This normalization procedure enabled direct comparison among the different wavelengths and was repeated prior to each measurement to minimize the impact of any drift in the circuit.

Test Methodology

Testing was conducted on three sets of porcine tissue harvested within 30 hours of the tests through Animal Biotech Industries (Danboro, Pa., USA). To replicate a right angle probe that allows the light and the receiver to be directed perpendicular to the tissue, two tests were conducted with the probe perpendicular to the tissue. The captured reflectance from the tissue samples were investigated in two testing configurations: "intact" and "mounted". The "intact" configuration (FIG. 12) consisted of creating a hole 512 in each tracheal tube 511 and directing the probe 502 with LED 503 directly at the side wall of the tissue to replicate what a right angle probe would see. The "mounted" configuration (FIG. 13) involved dissecting the tracheal tissue 513 and laying it flat to allow control of the actual separation distance between the probe 500 and the tissue 513 using a mounted optical eye.

To prevent any cross contamination between measurements the probe was cleaned using isopropyl alcohol and lens tissue between measurements. In addition, the dark output was measured between each trial where each trial consisted of three measurements of different parts of the esophagus and trachea of the same pig for one of the test types above.

Results

Overall, combining the intact and mounted testing configurations, a total of 19 different measurements were taken for the three different trachea samples and 19 measurements for the three different esophagus samples. Each tissue sample was tested under intact and mounted configurations, with three trials with each configuration, with trial one consisting of four measurements and trials two and three consisting of three measurements each. The threshold was calculated to be 3.5 mV. Output voltages for $R_{561}$, $R_{543}$, and $R_{578}$ were recorded and compared for the voltage differentials, $\Delta R_{561,543}$ and $\Delta R_{561,578}$ (Equation 1). Table 2, below, shows the average differentials recorded for both the trachea and esophageal tissues for each of the intact and mounted configurations, along with the results of a Welch's t-test comparing the test configurations.

TABLE 2

Voltage Differentials for Tracheal and Esophageal Tissues during Intact and Mounted Prototype Tests

| | | Tracheal Tissue | | Esophageal Tissue | |
| --- | --- | --- | --- | --- | --- |
| | | $\Delta R_{561,543}$ | $\Delta R_{561,578}$ | $\Delta R_{561,543}$ | $\Delta R_{561,578}$ |
| Intact | Differential | 12.375 | 10.5 | −4.38 | −13.48 |
| | Std. Dev | 3.84 | 5.07 | 2.22 | 3.28 |
| Mounted | Differential | 13.19 | 13.06 | −1.11 | −4.42 |
| | Std. Dev | 5.04 | 6.19 | 3.27 | 8.68 |
| | p-value | 0.70 | 0.34 | 0.025 | 0.0146 |

Detection was categorized as a true positive if both differential voltages were greater than the threshold in tracheal tissue or both differential voltages less than the threshold value for esophageal tissue; a false negative if only one differential voltage greater than the threshold in tracheal tissue and a false positive if both differentials being greater than the threshold in esophageal tissue. Table 3 shows the total results from the 38 trials, consisting of 19 tracheal and 19 esophageal.

TABLE 3

True Positive, False Negative and False Positive test results for tracheal and esophageal tissues in both intact and mounted configurations.

| Tissue | True Positive | False Negative | False Positive | Total |
| --- | --- | --- | --- | --- |
| Trachea | 18 | 1 | 0 | 19 |
| Esophagus | 18 | 0 | 1 | 19 |

The total results showed one false negative (failure to detect tracheal tissue in the trachea) and one false positive (detecting trachea tissue in the esophagus), amounting to 36 successful classifications out of 38 trials, consisting of 19 tracheal and 19 esophageal.

Discussion

In comparing the "intact" versus the "mounted" tests, the data showed no significant difference for the tracheal tube trials, but did show a difference for the esophageal trials. In reviewing the data, we found an inconsistency with the pig 2 esophageal trials, where the "mounted" tests consistently showed no difference or positive differences for $\Delta R_{561,543}$ and $\Delta R_{561,578}$, which would be expected in the tracheal tissue. These findings led us to believe that the probe could have been contaminated from the tracheal trial immediately preceding. Further inspection of the results also showed that there had been some drift in the gain between the circuits, which would have affected the threshold value used to differentiate the true or false positives. We believe this drift occurrence also in part contributed to the significant difference seen from the p-value of the intact versus mounted configuration seen for pig 2 in the esophageal tissue. The three trials conducted under these conditions, which happened to be in the mounted configuration, generated the only positive differential values for the esophageal tissue.

With an overall tracheal versus esophageal detection rate of 36 out of 38 trials to include the pig 2 esophageal trials, and with a specific tracheal detection rate of 18 out of 19, our prototype demonstrated that the previously identified tracheal spectral characteristics can be utilized to distinguish the trachea from the esophagus using low-cost, basic components. We chose to compare the prototype's detection rate with that of non-physician providers for the one-sided binomial test due to our envisioned application of the prehospital setting, where there is a higher prevalence of non-physician providers. The test compared the 36 successful classifications out of 38 trial detections with an 82% success rate, derived from meta-analyses of prehospital ETI success rates by non-physician providers (See, for example, Wang, H. E., et al. "*Out-of-hospital airway management in the United States.*" Resuscitation 82(4), 378-385 (2011); and Lossius, H. M, Roislien, J., and Lockey, D. J., "*Patient safety in pre-hospital emergency tracheal intubation: a comprehensive meta-analysis of the intubation success rates of EMS providers,*" Critical Care 16(R24), 1 (2012)). The resultant p-value was 0.0229, thereby showing that our prototype's detection ability was statistically significant when compared to the success rate of current airway management interventions. Naturally, our biggest concern from the results was with the false positive, which is removed with the removal of the pig 2 trials, based on the analysis above, and leaving an even more significant result of 34 successes out of 35 trials.

While these results are promising, additional work with instrumentation may be helpful. One area of future work is the interface of the fiber optic probe with the tissue. As we discovered in preliminary investigations before the study, placing the probe into the intact tracheal tissue through the glottic opening, such as in bronchoscopy, did not capture sufficient reflection from the tissue lumen running parallel to the axis of the probe. On the other hand, the same placement in the esophagus rendered appropriate reflection intensities. We believe this stems from the collapsed nature of the smooth muscle-walled esophagus, thereby bringing the luminal tissue in closer proximity to the aperture of the probe. Conversely, the rigid structure of the trachea, due to the cartilaginous rings, does not allow for beneficial angles of light reflection toward the fiber optic aperture. Therefore, we modified the present methodology for the intact configuration (FIG. 12) to accommodate for this instrumentation challenge. Additionally, we also investigated the mounted configuration (FIG. 13), for both tissue types to serve as a controlled methodology for distance from tissue and to maximize reflection return intensities.

With the mounted results confirming that of the intact results, we plan to continue the studies intact with design modifications to enable maximal reflectance returns captured by the probes. A primary concern will be to configure a right-angle at the tip of the fiber probe, to provide a normal interface between the aperture and the tissue. Additionally, we hope to refine the circuitry to a more stable platform, such as on a PCB, in order to further minimize any gain drifts or ambient electrical interference.

Summary and Ongoing Work

Based upon our previous work describing a unique spectral character distinguishing tracheal from esophageal tissue, we developed a prototype using discrete, low-cost components that was successfully able to detect tracheal versus esophageal tissue at a detection rate comparable to the success rates in prehospital settings. These initial prototype results demonstrate a promising proof of concept and show promise for future prototype iterations. A second discrete component prototype is in development with the goal being greater sensitivity to be able to better distinguish between the tissues. This prototype will consist of discrete photodiodes mounted on the actual probe with filters attached. The overall dimensions of the new prototype are approximately 20 mm×7 mm×5 mm.

Although the prototype may be too large to fit down a trachea, a significant reduction in size can be achieved by utilizing a flexible printed circuit board with a thickness on the order of 0.1 mm, and replacing the 2 mm thick filters with ultra-thin glass with thin film optical filters placed over the photodiodes. Additionally, from the test results above, utilizing only the 561 nm band and the 543 nm band provide identical results, suggesting that only two filtered photodiodes would be needed. We expect dimensions of such a system to be further reduced to approximately 15 mm×3 mm×1.5 mm. Even further reductions in size can be made by building the entire circuit on a single substrate (although the LED would likely have to be wafer bonded).

Alongside prototype improvements, we plan to test the second generation prototype in fresh frozen human cadaver models to overcome the present limitation of using swine tissue. Preliminary, informal investigations using spectrometers and fiber-optic probes have confirmed the spectral similarities between human and swine tracheal and esophageal tissues.

Additional Research and Testing

Back-End Filtering Prototype Development

Based on the initial promising results from the tracheal detection using the comparison of relative intensities at 543 nm, 561 nm and 578 nm, a next-generation prototype was designed for the LED and fiber-optic configuration to optimize for right angle sensing (FIG. 16B). A plastic optical fiber was utilized to create a 90-degree bend at the distal sensing end and epoxied into a hole drilled into a printed circuit board (PCB). Two white LED's were configured to each side of the fiber optic to provide broadband tissue illumination. The entire distal sending end measured approximately 15 mm×7 mm×5 mm. The same glass filters (Table 1 above), photodiode instrumentation (FIG. 10) and interpretation circuitry (FIG. 14) were used. Five separate ex vivo pig trachea samples were obtained and tested by inserting the probe into the trachea in a similar fashion as a bronchoscope, endotracheal tube, or bougie. A rigid wire was fastened alongside the plastic optical fiber and the electrical wires that extend back to the circuitry to provide more physical rigidity to the device as it is introduced into the tissue.

Output voltage measurements were taken at variable depths throughout the trachea and detection was determined by ratio detection algorithms shown in Equations 3(a) (Ratio B) and 3(b) (Ratio Y) above. Table 4 shows the detection results calculated from each of the ratios.

TABLE 4

|  | Total Trials | Ratio B | Ratio Y |
| --- | --- | --- | --- |
| Tissue 1 | 24 | 22 | 24 |
| Tissue 2 | 22 | 21 | 22 |
| Tissue 3 | 24 | 19 | 24 |
| Tissue 4 | 23 | 17 | 23 |
| Tissue 5 | 23 | 8 | 23 |
| TOTALS | 116 | 87 | 116 |

While these preliminary results show Ratio Y as a stronger predictor of detection, there was a persistently weaker signal coming from the circuitry used to amplify the 543 nm signal used in the Ratio B calculation. As prototyping continues to more robust designs and platforms we anticipate that the signal fidelity will be stronger and, thus, the Ratio B calculation may perform better. However, these results suggest that the optimization for right-angle sensing and the ratio detection algorithm approach are promising embodiments of the Back-End filtering prototype.

In Vivo Swine Vs. Human Cadaver Testing

For both swine and cadaver tests, reflectance spectra were captured using a fiber optic reflection probe connected to a compact spectrometer and a white light source, as instrumented in our previous it situ studies (Nawn, C. D., Souhan, B., Carter, R., Kneapler, C., Fell, N., & Ye, J. Y. (2016). "Distinguishing tracheal and esophageal tissues with hyperspectral imaging and fiber-optic sensing." *Journal of biomedical optics*, 21(11), 117004). Our prior work identified the particular region of interest to be 500 nm to 650 nm. Therefore, the white light source was chosen to optimize the output in that particular region and the fiber optic probe was a customized 200-μm core, 2 meter long bifurcated probe with a prism at the distal end to enable 90 degree illumination and capture. The distal tip of the probe included a rounded metal tip encapsulated with epoxy to prevent tissue damage upon insertion and removal.

Spectral Data Analysis

The reflectance, absorbance, and amplitude spectra for both human cadaver and swine tests were collected through the SpecSoft Software, stored as text files and imported into MATLAB for spectral analysis. Each pig and cadaver was numerically identified as 1 through 8 with additional identification of spectra with respect to the tissue type: tracheal and esophageal. For the purposes of data analysis and direct comparison with cadaver data, the present study solely analyzed the three baseline periods (i.e., those points at which the airway was not obstructed) to limit potential unknown effects of hypoxia on the tissue reflectance properties.

All tracheal and esophageal spectra, both pig and human cadaver, were plotted separately to inspect for signal fidelity or any erroneous captures. Based on previous work characterizing the particular unique characteristic in the 500 nm to 650 nm range, all spectra were cropped to focus on this region of interest. The mean value was subtracted from each spectrum to establish the same baseline for more direct comparison. Data were then smoothed in MATLAB using a moving average filter to attenuate the noise inherent in in vivo captures. To qualitatively compare spectra among pig and cadaver subjects, reflectance spectra for each subject's trachea and esophagus were averaged by summing the value at each data point across the captured profiles and dividing by the number of profiles in order to arrive at one reflectance spectrum representing the trachea and one reflectance spectrum representing the esophagus for each subject. The averaged reflectance spectra for subjects were then plotted simultaneously, within species and tissue type, to inspect for and compare any differences in spectral characteristics.

With the ultimate application of leveraging the unique spectral characteristic for the purpose of tracheal detection in airway management, comparisons were done to evaluate whether the relative prominence of the tracheal peak could distinguish tracheal from esophageal captures. The amplitude values at 543 nm, 561 nm, and 578 nm were extracted from each capture and plotted, using boxplots, to visualize the distribution. Based on the nonparametric distribution, the Wilcoxon Signed Rank Sum test was subsequently used in the comparisons between tissue types within species, and the Wilcoxon Rank Sum test was used for comparisons within tissue type between species. The wavelengths 543 nm, 561 nm, and 578 nm were chosen based upon commercially available glass filters in order to represent a detection algorithm that could be implemented by developed prototypes.

In addition to investigating the difference between tissue types in absolute amplitudes of the peak, we also calculated ratios for detection in order to account for the relative intensity of the signal. The ratio detection algorithm in Equation 3(a) (above) compares the reflectance captured at 561 nm (R561) versus the reflectance at 543 nm (R543) for Ratio "B." The ratio detection algorithm in Equation 3(b) (above) compares the reflectance captured at 561 nm (R561) versus the reflectance at 578 nm (R578) for Ratio "Y". Ratio "B" was termed based on 543 nm being approximately blue light, while Ratio "Y" was termed as such from 578 nm being approximately yellow light in the visible spectrum.

The ratios were calculated for each spectrum capture for all tracheal and esophageal data and then plotted simultaneously to find natural cut points to determine a threshold difference range between tissue types. A ratio was determined as a tracheal detection if it exceeded the upper threshold, while it was termed as an esophageal detection if it was below the lower threshold. The small gap between the upper and lower threshold points represent a region of uncertainty where the ratio cannot be definitively indicative of either tissue type. Sensitivity, Specificity and Positive Predictive Value (PPV) was then calculated based on the comparisons between the tissue type as determined by the ratio detection versus the true tissue type.

Results

In Vivo Swine Results

Figure 17A:
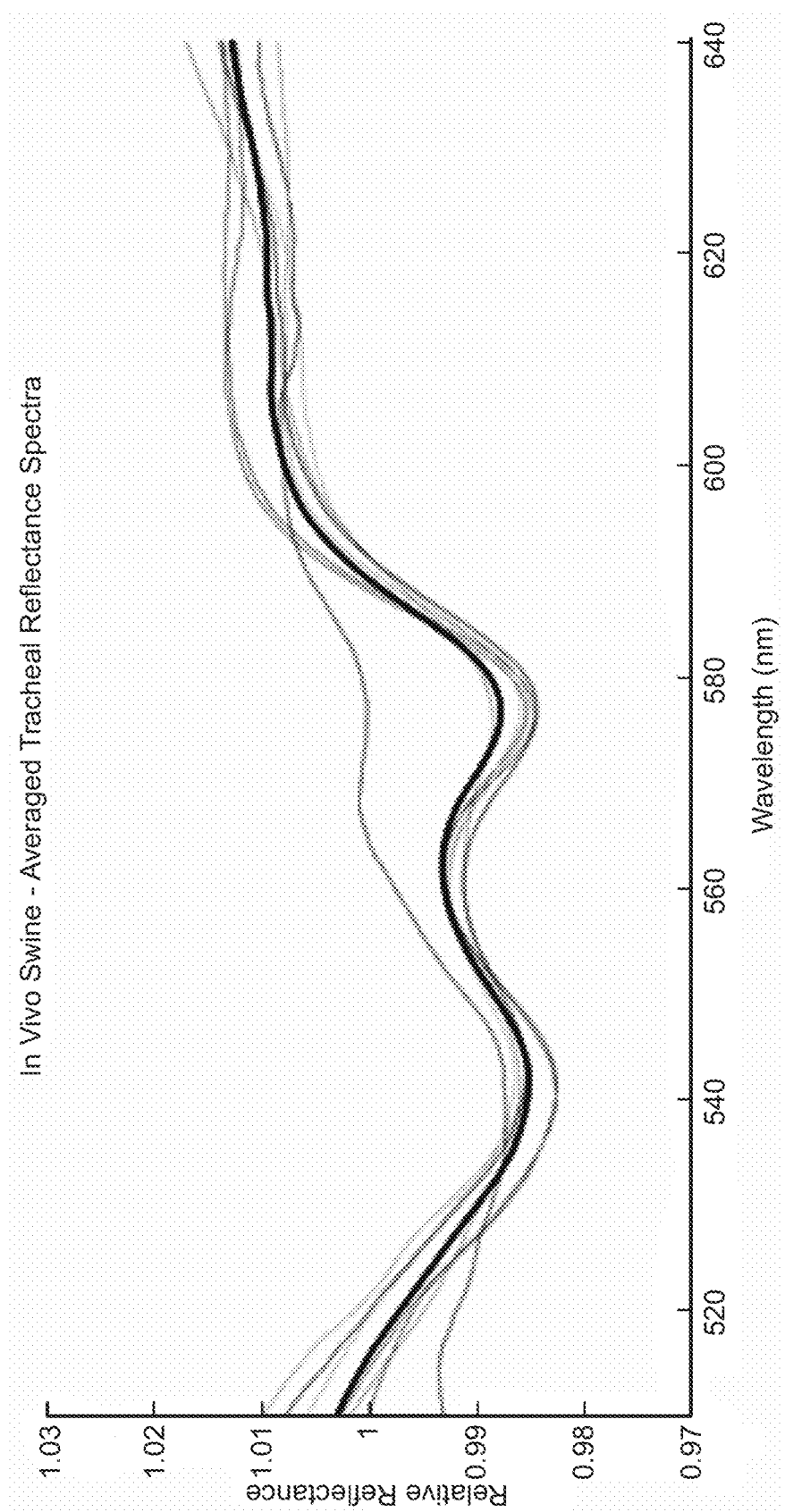
FIG. 17A is a plot of averaged relative reflectance vs. wavelength for seven porcine tracheae.
Figure 17B:
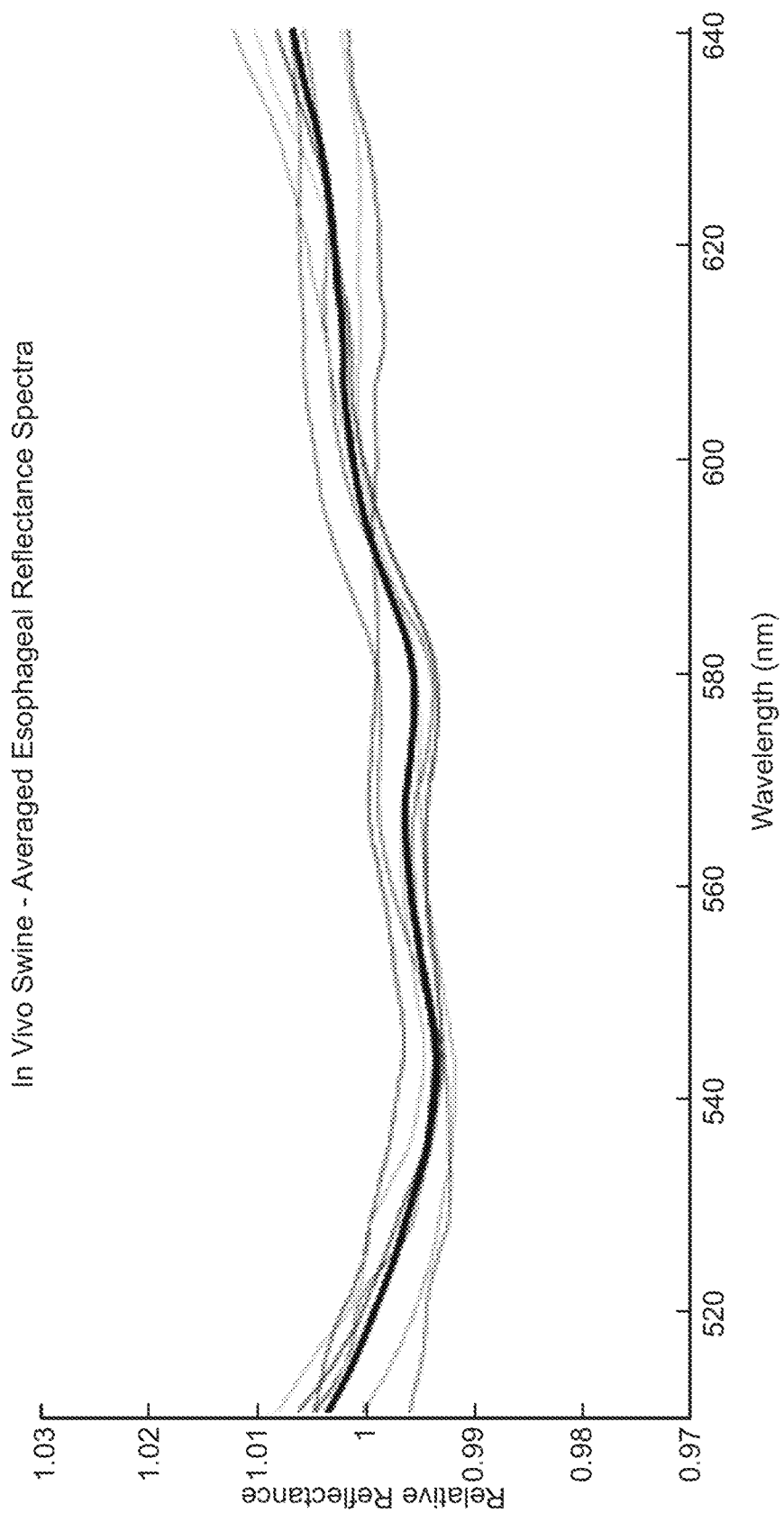
FIG. 17B is a plot of averaged relative reflectance vs. wavelength for seven porcine esophagi.

Spectral data were collected on eight pigs. Five spectral captures were taken in the trachea and esophagus during each of three baseline periods, totaling 15 captures in each trachea and esophagus per pig. One pig's spectral data was discarded during post-collection data analysis due to improper calibration, yielding seven complete sets of in vivo swine captures. FIG. 17A is a plot of averaged relative reflectance vs. wavelength for seven pigs' tracheae. FIG. 17B is a plot of averaged relative reflectance vs. wavelength for seven pigs' esophagi. In FIGS. 17A and 17B, the thin lines represent averaged spectra for each individual pig (n=7) and the heavy black line represents the average of all seven pigs.

Tracheal spectra (FIG. 17A) generally exhibit the same peak as previously described (Nawn et al, 2017), with local minima around 543 nm and 578 nm and a local maximum around 561 nm. The esophageal data (FIG. 17B) also display a slight peak with similar characteristics; however, when juxtaposed to the tracheal spectra, the feature appears less prominent in amplitude. To quantitatively compare the differences in spectra with respect to the wavelengths of interest, reflectance values at 543 nm, 561 nm, and 578 nm were extracted from each capture (n=105). The reflectance values at all three wavelengths were significantly different between trachea and esophagus as shown in Table 5. below.

TABLE 5

Comparison of Swine Tracheal vs. Esophageal Reflectance (n = 105)

| Wavelength | Tracheal Reflectance Median and IQR | Esophageal Reflectance Median and IQR | p-value |
| --- | --- | --- | --- |
| R543 | 0.985 (0.005) | 0.993 (0.003) | <0.001 |
| R561 | 0.993 (0.004) | 0.996 (0.003) | <0.001 |
| R578 | 0.988 (0.005) | 0.995 (0.004) | <0.001 |

Human Cadaver Results

Figure 18A:
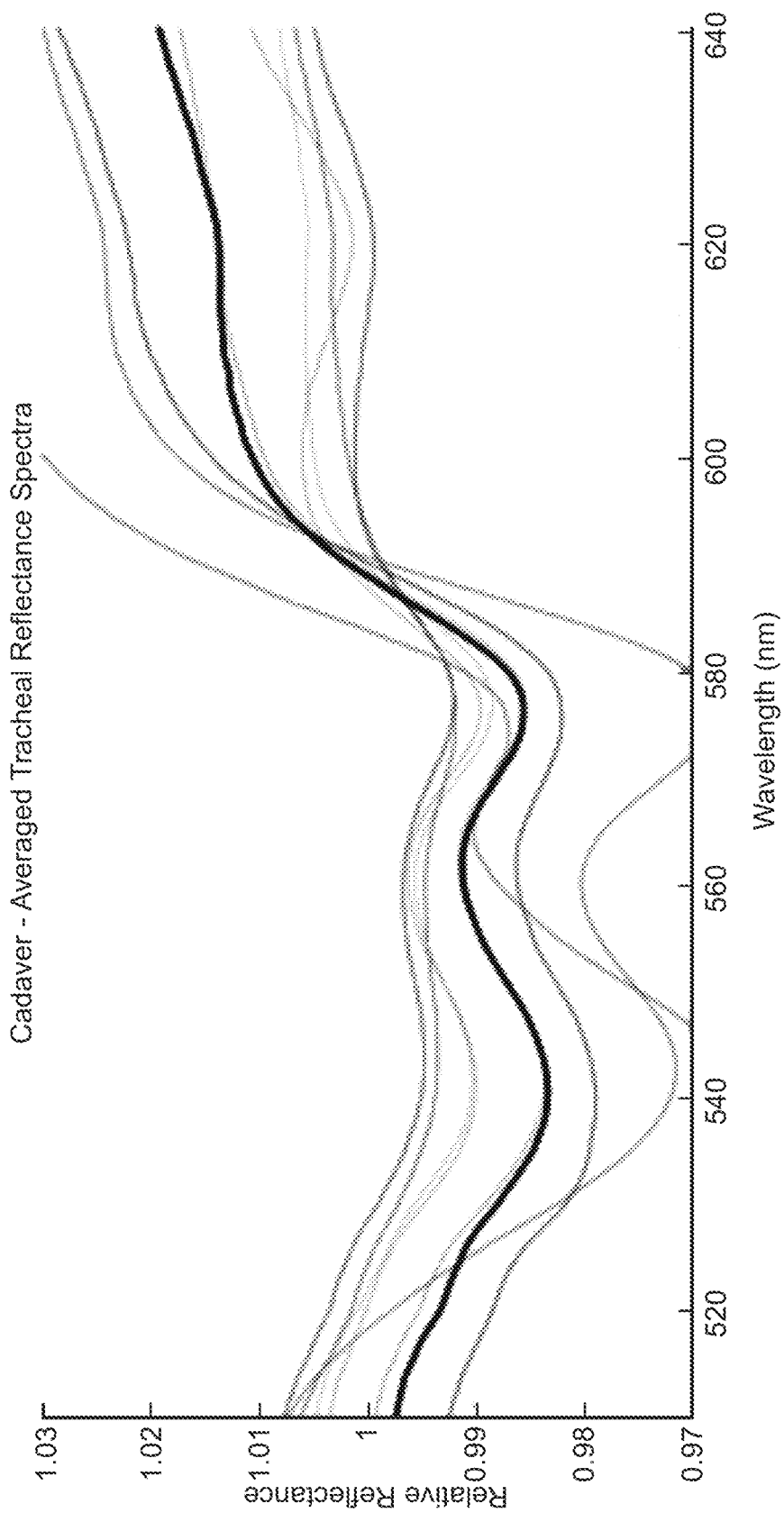
FIG. 18A is a plot of averaged relative reflectance vs. wavelength for eight human trachea.
Figure 18B:
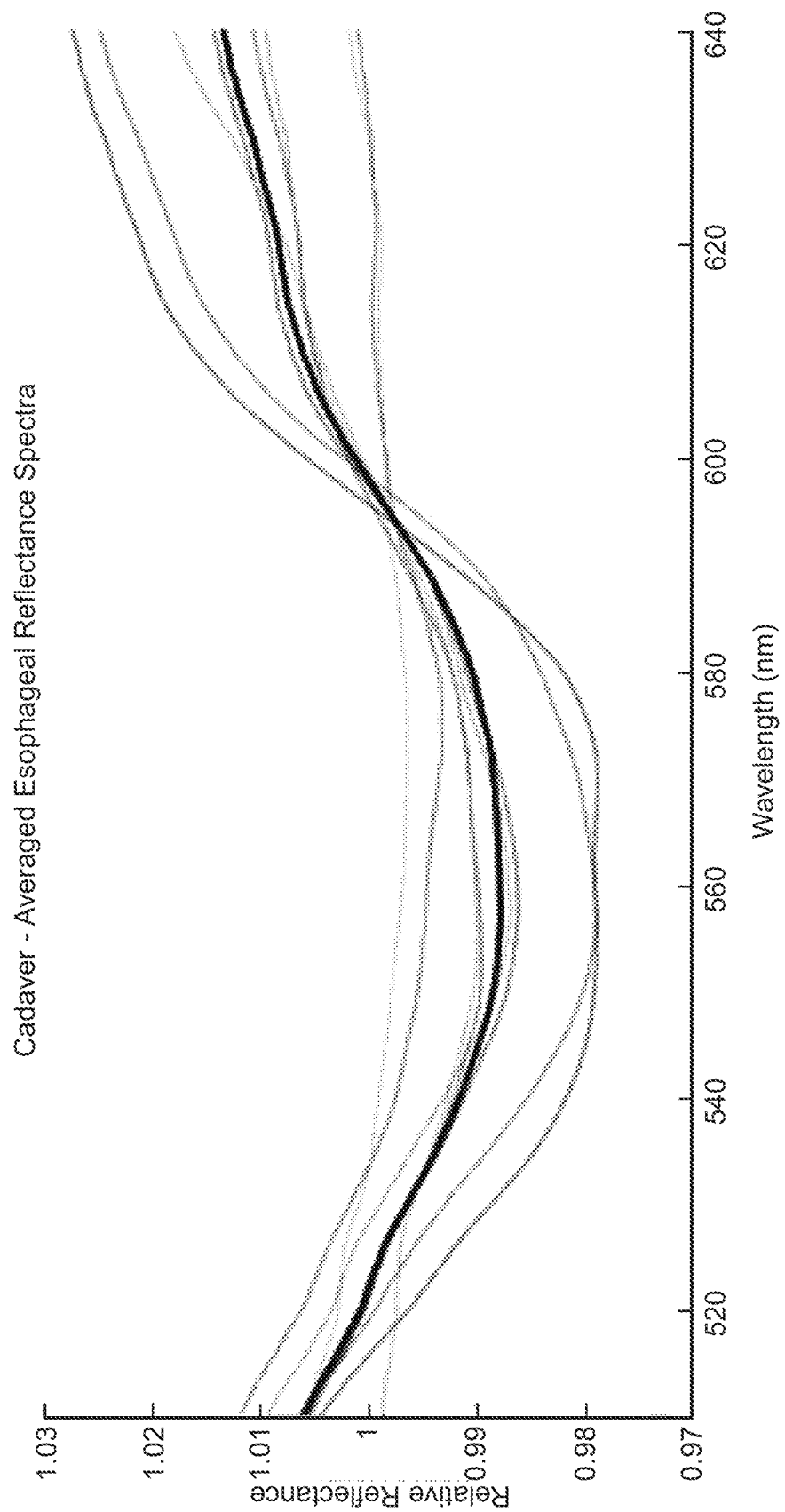
FIG. 18B is a plot of averaged relative reflectance vs. wavelength for eight human esophagi.

Spectral captures in both the trachea and esophagus were collected on eight human cadavers with mixed demographics. Five captures in each trachea and esophagus were taken per cadaver, yielding a total of 40 captures. FIGS. 18A and 18B show the averaged tracheal and esophageal spectra, respectively, for each cadaver, with the overall average for all captures shown in a heavy line. In FIGS. 18A and 18B, the thin lines represent averaged spectra for each individual human cadaver (n=8) and the heavy black line represents the average of all eight human cadavers.

Qualitative analysis of the human cadaver results confirms the existence of the tracheal peak, with minima around 543 nm and 578 nm and maximum around 561 nm. The esophageal spectra closely mirrored previous findings, exhibiting a more gradual negative slope over the region of interest without any peak. Reflectance values at all three wavelengths were significantly different between trachea and esophagus as shown in Table 6 below.

TABLE 6

Comparisons of Cadaver Tracheal vs. Esophageal Wavelength Measures (n = 40).

| Wavelength | Tracheal Reflectance Median and IQR | Esophageal Reflectance Median and IQR | p-value |
|---|---|---|---|
| R543 | 0.987 (0.020) | 0.993 (0.012) | <0.001 |
| R561 | 0.993 (0.008) | 0.990 (0.011) | <0.001 |
| R578 | 0.989 (0.007) | 0.993 (0.008) | <0.001 |

Figure 19:
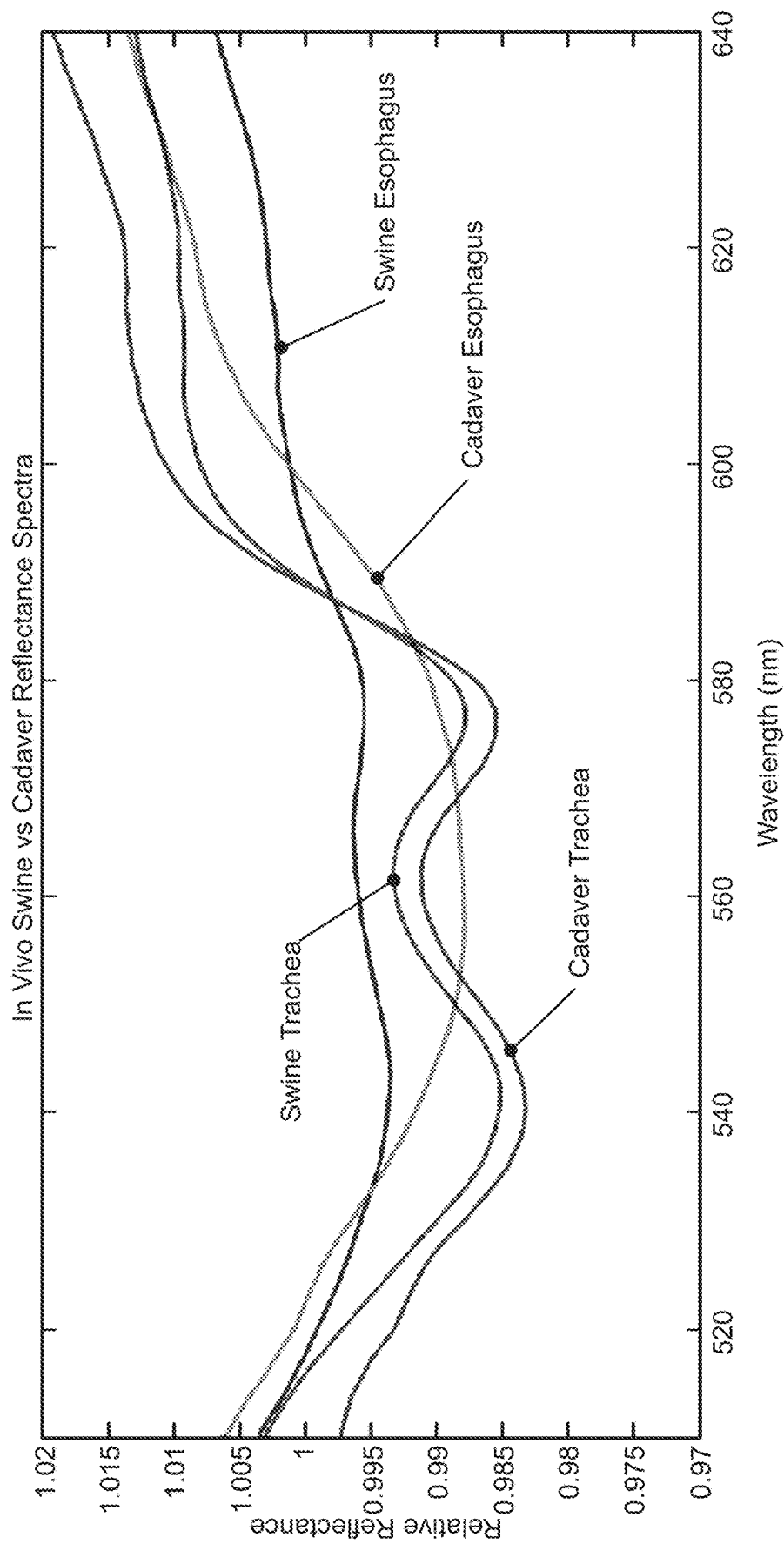
FIG. 19 is a plot of averaged relative reflectance vs. wavelength for tracheal and esophageal tissue from swine and human cadavers.

FIG. 19 shows the juxtaposed tracheal and esophageal averaged spectra from the swine and human cadavers. There was no significant difference (p>0.23) in the absolute tracheal reflectances at any of the 3 wavelengths between the in vivo pigs and human cadavers. The characteristic reflectance spectrum of the trachea was thus exhibited in both species.

Tracheal Detection Tests

Figure 20A:
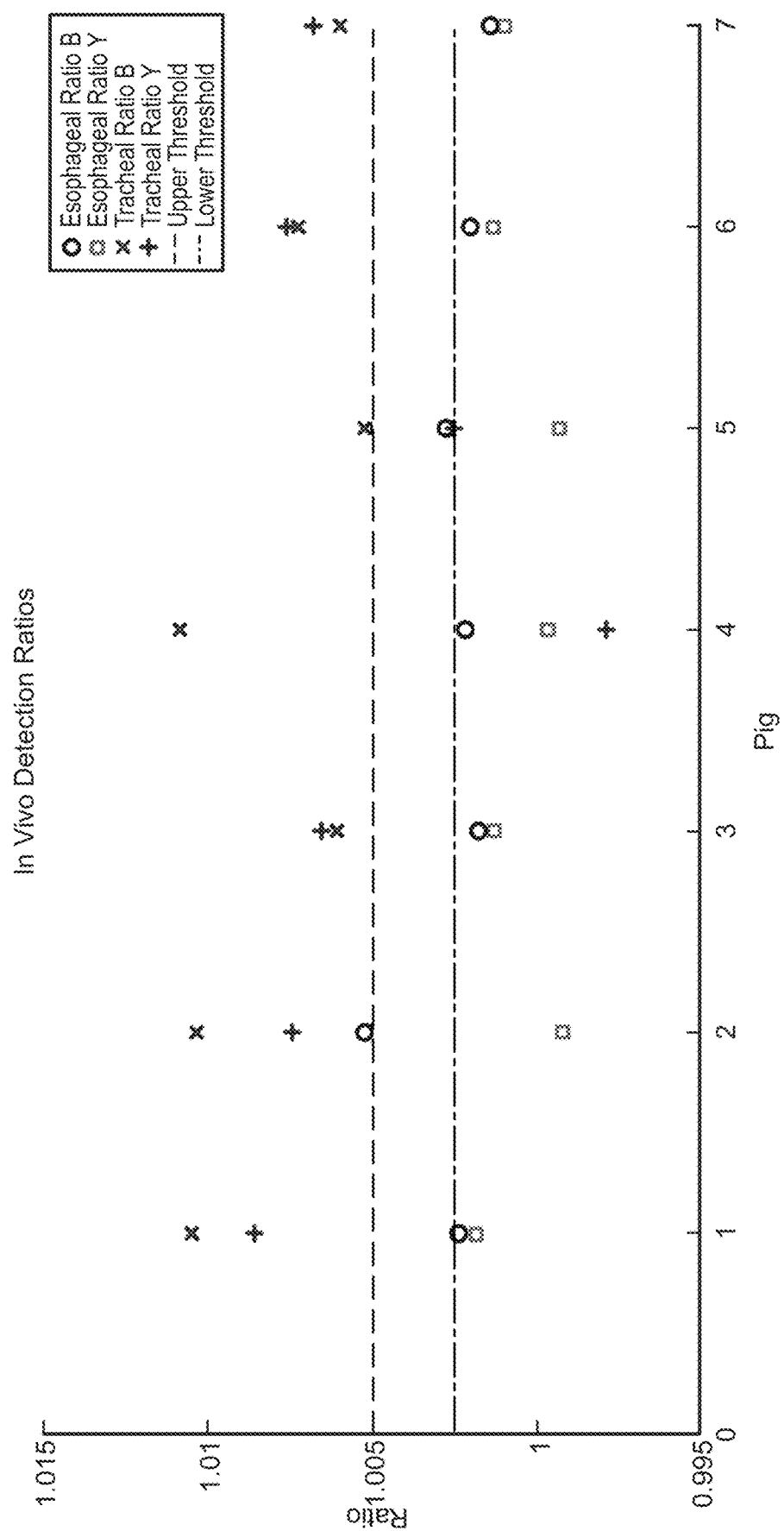
FIG. 20A is a plot of detection ratios B and Y for tracheal and esophageal tissue in seven pigs.
Figure 20B:
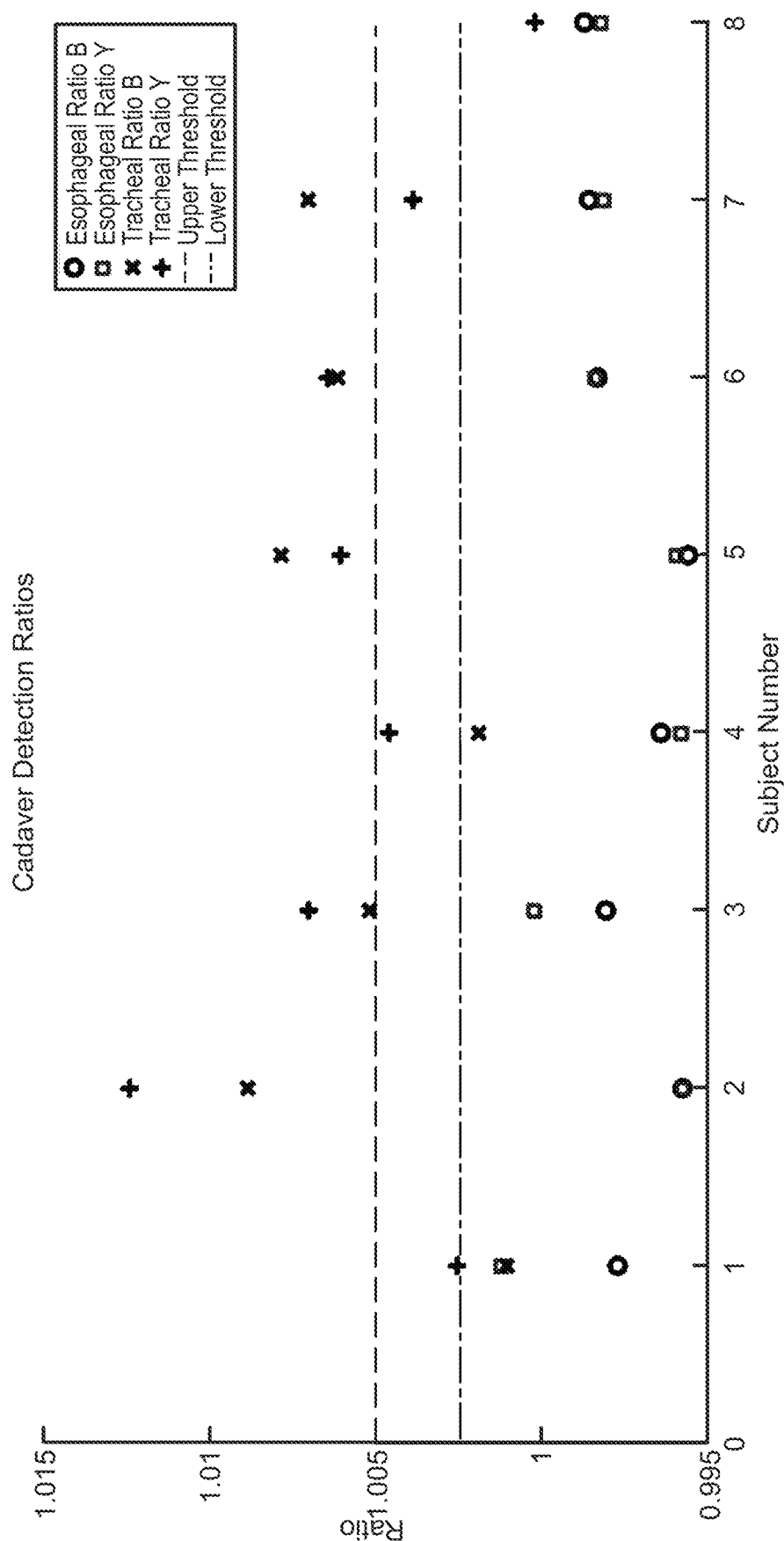
FIG. 20B is a plot of detection ratios B and Y for tracheal and esophageal tissue in eight human cadavers.

With the ultimate application of leveraging the unique spectral characteristic for tracheal detection, we also evaluated whether the relative prominence of the tracheal peak could distinguish tracheal from esophageal tissue. The detection ratios, ratio B and ratio Y (Equations 3(a) and 3(b)), were calculated for each capture in swine (n=105) and human cadavers (n=40). All values were plotted and the lines of best delineation between the tracheal and esophageal ratio points were determined from observation; these were termed "upper threshold" and "lower threshold". The ratios were then averaged, to yield an average tracheal ratio B, tracheal ratio Y, esophageal ratio B, and esophageal ratio Y for each pig and cadaver subject (FIGS. 20A and 20B). FIG. 20A is a plot of detection ratios B and Y for tracheal and esophageal tissue in seven pigs. FIG. 20B is a plot of detection ratios B and Y for tracheal and esophageal tissue in eight human cadavers. Dashed lines indicate upper and lower threshold values.

For each individual capture, the ratios above the upper threshold (1.005) were termed as a positive tracheal detection and below the lower threshold (1.0025) were termed as an esophageal detection. The gap between the upper and lower thresholds provides a buffer between the positive and negative detection where the data may not confidently predict tracheal or esophageal. Using these determinations, the sensitivity, specificity, positive predictive values and negative predictive values were calculated for Swine Ratio B, Swine Ratio Y, Cadaver Ratio B, and Cadaver Ratio Y (Table 7).

TABLE 7

Sensitivity, Specificity, Positive Predictive Values (PPV) for Swine and Cadaver Ratios

| | Sensitivity | Specificity | PPV |
|---|---|---|---|
| Swine Ratio B | 97% | 85% | 88% |
| Swine Ratio Y | 81% | 100% | 100% |
| Cadaver Ratio B | 69% | 100% | 100% |
| Cadaver Ratio Y | 65% | 100% | 100% |

Discussion

The previously identified unique spectral characteristics of tracheal tissue are still present and able to distinguish tracheal tissue from esophageal in both in vivo swine and human cadavers. Both the qualitative and quantitative assessments of the tracheal versus esophageal spectra, within each species, support the uniquely differentiating ability of the reflectance at 543 nm, 561 nm and 578 nm. Furthermore, the characteristics of this feature allow the tracheal tissue to be distinguished from esophageal tissue, as evidenced by the strong positive-predictive values of Ratios B and Y. The persistence of this spectral characteristic across species indicates that this measurement may be clinically useful in determining proper placement of an endotracheal tube.

We had previously demonstrated differences in spectral characteristics between tracheal and esophageal tissue in ex vivo swine tissues (Nawn et al, 2016, supra). In the current study, this same spectral signature was exhibited by human cadavers, indicating that it persists across species. These differences were also evident in living swine, showing that the spectral signatures are inherent to the tissue themselves, regardless of perfusion status of the tissues. Qualitatively, the tracheal reflectance spectra appeared very similar between swine and human cadavers, while the esophageal spectra in vivo swine exhibited a vague peak in the same range as that of the distinguishable tracheal peak (FIG. 19). Quantitatively, the similarity of the tracheal spectra was supported by the lack of significance when comparing the reflectance at the target wavelengths of 543 nm, 561 nm, and 578 nm. Conversely, the comparisons between species for the esophageal spectra at these wavelengths did produce a significant difference at 561 nm and 578 nm.

While absolute reflectance values differed between the two tissue sites, we also sought to emphasize the prominence of the tracheal peak relative to that produced by the esophagus by calculating the Ratio B and Ratio Y. From these results, Ratio Y demonstrates a higher positive predictive value in both swine and cadavers. However, Ratio B exhibited a greater sensitivity for detecting the trachea correctly in perfused swine. Clinically, these ratios have translational application in that they could be incorporated as detection logic in an airway device for the purpose of rapid tracheal detection. The performance comparison of these two ratios could inform device design choices. As mentioned in the methods, the wavelength selections were based on commercially available filters that could be employed using photodetectors or fiber optics to isolate the target wavelengths for the ratio comparison. While both ratios use the peak wavelength at 561 nm in the comparison, Ratio B compares the center versus 543 nm whereas Ratio Y compares the center versus 578 nm. Thus, three filters would be required to capture and utilize both ratios for detection. In practical implementation, this becomes a design tradeoff based on the size of the components and logic and the placement of each. For example, a device that filters the wavelength immediately upon capture of the light would place the filters at the distal tip of the device that would be in contact with the patient. Some implementations may elect to reduce the size of a sensor placed in this fashion in order to keep the overall device design as minimally invasive as possible. Thus, the design choice may involve choosing only one of the ratios and thereby only requiring two filters. On the other hand, if the device were to collect and transmit all reflected light to a filtering platform situated more proximally to the external end of the device, there may be more available real estate to employ three filters and the matching logic to make use of both ratios. The advantage of using both ratios would be in providing detection redundancy to increase the strength of the predictive value.

Given these design considerations, both "front-end" and "back-end" filtering approaches could be implemented in endotracheal devices known prior to the instant invention. Endotracheal tubes could have photodetectors with filters or a fiber optic incorporated at the distal tip, inside, within, or outside the lumen. If the "front-end" filtering approach is employed, the captured light will be converted to a voltage at the site of the collection with the filter and photodetector, and the voltage transmitted to the proximal end for comparison logic to determine the ratios and distinguish the predicted tissue. Alternatively, the "back-end" filtering would collect and transmit all light, such as through a fiber-optic, to the proximal end where the filters and comparison logic will both be situated thereby enabling the bulkier components to be located farther from the portion in contact with the patient.

FIG. 16A is a schematic diagram of an embodiment of a "front-end" filtering apparatus for an airway management device. A powering signal 700 is transmitted to the light-emitting elements 701 on the probe that illuminate the tissue 702 with visible light 703. The light 703 then interacts with the tissue 702 and reflects a reflectance spectrum 704, which is captured by photo-sensing elements 705 that then filter the specified wavelengths of interest. For this implementation, the wavelengths of interest may be around 540 nanometers, 560 nanometers, or 578 nanometers. The relative intensities of these captured wavelengths are then transmitted back to the detection circuitry as a voltage 706.

FIG. 16B is a schematic diagram of an embodiment of a "back-end" filtering apparatus for an airway management device. A powering signal 710 is transmitted to the light-emitting elements 711 on the probe that illuminate the tissue 712 with visible light 713. The light 713 then interacts with the tissue 712 and reflects a reflectance spectrum 714, which is captured by a photo-sensing element 715, such as a fiber-optic shown in this implementation. The captured reflectance spectrum is then transmitted back as a spectrum 716 to be filtered and converted to voltage for comparison by the detection circuitry.

Conclusion

Overall, the present study validates the previously observed unique spectral reflectance characteristic of tracheal tissue in vivo swine and human cadaver models. Within each of these models, the data support the ability to differentiate between tracheal and esophageal tissue types by comparing the reflectance at approximately 543 nm, 561 nm and 578 nm. While the present study captured and investigated the full spectra, the analysis aimed to focus on specific wavelengths that could be filtered and compared using discrete components for the purpose of simulating logic that could be employed in a device. The clinical significance of these findings is in leveraging the comparisons of these wavelengths to be utilized as potential differentiators between esophageal and tracheal tissue. As discussed, the design tradeoffs in implementing this approach lend itself well to efficient integration into existing airway technologies and techniques to enable rapid tracheal confirmation during procedures and throughout transport. Given the importance of rapid and accurate identification of the trachea during airway management, especially in pre-hospital situations, incorporating such a tracheal detection approach could aid in immediate feedback to the provider thereby enabling faster times to securement. Furthermore, with the ability to be integrated into airway devices, this approach could provide a small and portable technology for continuous monitoring to ensure proper tracheal tube placement such as during transport when dislodgement can occur.

Embodiments of the invention have been described to explain the nature of the invention. Those skilled in the art may make changes in the details, materials, steps and arrangement of the described embodiments within the principle and scope of the invention, as expressed in the appended claims.

What is claimed is:

1. An airway management device for a human or animal subject, comprising:
   an endotracheal tube having a first end for disposal external to the subject and a second end for disposal in a trachea of the subject;
   a light emitting element and a photo-sensing element disposed at the second end of the airway tube;
   the light emitting element being configured to transmit light to tissue adjacent to the light emitting element and the photo-sensing element being configured to receive reflectance spectra from the tissue;
   wherein a location of the second end of the endotracheal tube in one of the trachea and an esophagus of the subject is determined by a signal processor or a spectrum analyzer from intensities of the reflectance spectra received by the photo-sensing element across a range of wavelengths.

2. The device of claim 1, further comprising at least one signal conduit within or adjacent the endotracheal tube, the at least one signal conduit being integral with or connected to the light emitting element and the photo-sensing element.

3. The device of claim 2, further comprising the signal processor connected to the photo-sensing element via the signal conduit for processing the reflectance spectra from the tissue.

4. The device of claim 2, further comprising the spectrum analyzer connected to the photo-sensing element via the signal conduit for processing the reflectance spectra from the tissue.

5. The device of claim 2, wherein the light emitting element includes a light source.

6. The device of claim 2, further comprising a light source connected to the light emitting element and configured for disposal external to the subject.

7. The device of claim 3, wherein the signal conduit is one of an electrical and optical signal conduit.

8. The device of claim 4, wherein the signal conduit is an optical signal conduit.

9. The device of claim 1, wherein the range of wavelengths are in the visible light spectrum.

10. The device of claim 9, wherein the range of wavelengths is from 500 nanometers to 590 nanometers.

11. The device of claim 10, wherein the range of wavelengths is from 530 nanometers to 580 nanometers.

12. The device of claim 11, wherein the tissue is tracheal tissue and, as wavelengths of the reflectance spectra increase, the intensities of the reflectance spectra include a first minimum reflectance followed by a maximum reflectance followed by a second minimum reflectance.

13. The device of claim 12, wherein the maximum reflectance is at about 560 nanometers.

14. A method of positioning an endotracheal tube in an airway of a human or animal subject, comprising:
inserting a distal end of the endotracheal tube in one of a trachea and an esophagus of the subject;
illuminating tissue around the distal end of the endotracheal tube with visible light;
collecting a reflectance spectrum from the tissue; and
comparing the reflectance spectrum to a characteristic reflectance spectrum to determine if the distal end is in the trachea or the esophagus.

15. The method of claim 14, further comprising, before the step of inserting, determining the characteristic reflectance spectrum from one or more tissue samples from a second human or animal subject.

16. The method of claim 15, wherein the characteristic reflectance spectrum is taken from tracheal tissue samples.

17. The method of claim 16, where the step of comparing includes comparing intensities of the reflectance spectrum to intensities of a characteristic reflectance spectrum having a wavelength range of 500 nanometers to 590 nanometers.

18. The method of claim 17, wherein the step of comparing includes comparing intensities of the reflectance spectrum to intensities of a characteristic reflectance spectrum having a wavelength range of 530 nanometers to 580 nanometers.

19. The method of claim 18, wherein the step of comparing includes comparing the intensities of the reflectance spectrum to intensities of a characteristic reflectance spectrum having, in a direction of increasing wavelength, a first minimum reflectance followed by a maximum reflectance followed by a second minimum reflectance.

20. The method of claim 19, wherein the maximum reflectance is at about 560 nanometers.

21. A method of positioning an endotracheal tube in an airway of a human or animal subject, comprising:
inserting a distal end of the endotracheal tube in one of a trachea and an esophagus of the subject;
illuminating tissue around the distal end of the endotracheal tube with visible light;
collecting reflectance intensity of at least one wavelength from the tissue; and
comparing the reflectance intensity to a characteristic reflectance intensity to determine if the distal end is in the trachea or the esophagus.

22. The method of claim 21, further comprising, before the step of inserting, determining the characteristic reflectance intensity from one or more tissue samples from a second human or animal subject.

23. The method of claim 22, wherein the characteristic reflectance intensity is taken from tracheal tissue samples.

24. The method of claim 23, where the step of collecting includes collecting reflectance intensity at one or more of 543 nm, 561 nm and 578 nm wavelengths.

25. The method of claim 24, wherein the step of comparing includes comparing reflectance intensity at one or more of 543 nm, 561 nm and 578 nm wavelengths to characteristic reflectance intensity at one or more of 543 nm, 561 nm and 578 nm wavelengths.

26. The method of claim 25, wherein the step of comparing includes comparing a reflectance intensity ratio of 561 nm to 578 nm to a characteristic reflectance intensity ratio of 561 nm to 578 nm.

27. The method of claim 24, wherein the step of comparing includes comparing a reflectance intensity ratio of 561 nm to 543 nm to a characteristic reflectance intensity ratio of 561 nm to 543 nm.

28. An airway management device for a human or animal subject, comprising:
an endotracheal tube having a first end for disposal external to the subject and a second end for disposal in one of a trachea and an esophagus of the subject;
a light emitting element and a photo-sensing element disposed at the second end of the endotracheal tube tube;
the light emitting element being configured to transmit light to tissue adjacent to the light emitting element and the photo-sensing element being configured to receive reflectance intensity from the tissue;
wherein a location of the second end of the endotracheal tube in the one of the trachea and the esophagus of the subject is determined by a signal processor from the reflectance intensity received by the photo-sensing element at at least one wavelength.

29. The device of claim 28, further comprising at least one signal conduit within or adjacent the endotracheal tube, the at least one signal conduit being integral with or connected to the light emitting element and the photo-sensing element.

30. The device of claim 29, further comprising the signal processor connected to the photo-sensing element via the signal conduit for processing the reflectance intensity from the tissue.

31. The device of claim 29, wherein the light emitting element includes a light source.

32. The device of claim 29, further comprising a light source connected to the light emitting element and configured for disposal external to the subject.

33. The device of claim 29, wherein the signal conduit is one of an electrical and optical signal conduit.

34. The device of claim 28, wherein the at least one wavelength includes one or more of 543 nm, 561 nm and 578 nm wavelengths.

35. The device of claim 34, wherein the tissue is tracheal tissue.

* * * * *